United States Patent
Czirok et al.

(10) Patent No.: US 12,281,333 B2
(45) Date of Patent: Apr. 22, 2025

(54) RENAL TUBE ASSAY DEVICE AND METHODS OF MANUFACTURE AND USE

(71) Applicant: The University of Kansas, Lawrence, KS (US)

(72) Inventors: Andras Czirok, Roeland Park, KS (US); Pamela Tran, Overland Park, KS (US)

(73) Assignee: UNIVERSITY OF KANSAS, Lawrence, KS (US)

( * ) Notice: Subject to any disclaimer, the term of this patent is extended or adjusted under 35 U.S.C. 154(b) by 352 days.

(21) Appl. No.: 17/518,395

(22) Filed: Nov. 3, 2021

(65) Prior Publication Data

US 2022/0135951 A1    May 5, 2022

Related U.S. Application Data

(60) Provisional application No. 63/109,630, filed on Nov. 4, 2020.

(51) Int. Cl.
| | |
|---|---|
| *C12N 5/071* | (2010.01) |
| *C12M 1/12* | (2006.01) |
| *C12M 1/34* | (2006.01) |
| *C12M 3/06* | (2006.01) |
| *G01N 33/50* | (2006.01) |

(52) U.S. Cl.
CPC .......... *C12N 5/0686* (2013.01); *C12M 23/06* (2013.01); *C12M 23/16* (2013.01); *C12M 41/36* (2013.01); *C12M 41/46* (2013.01); *G01N 33/5044* (2013.01)

(58) Field of Classification Search
CPC .............. C12N 5/0686; C12N 2513/00; C12N 2533/54; C12N 2533/56; C12M 23/06; C12M 23/16; C12M 41/36; C12M 41/46; C12M 25/14; G01N 33/5044
See application file for complete search history.

(56) References Cited

U.S. PATENT DOCUMENTS

| | | | |
|---|---|---|---|
| 10,702,630 B2 * | 7/2020 | Lewis ................. | A61L 27/3891 |
| 2015/0087004 A1 * | 3/2015 | Chen ...................... | C12M 25/14 435/402 |
| 2017/0009194 A1 * | 1/2017 | Golway ............. | G01N 33/5064 |

OTHER PUBLICATIONS

Supplemental Information for Homan et al. 2016. "Bioprinting of 3D Convoluted Renal Proximal Tubules on Perfusable Chips". Sci Rep 6, 34845. 13 pages total. https://doi.org/10.1038/srep34845 (Year: 2016).*
Sullivan et al. 1998. "Epithelial transport in polycystic kidney disease". Physiological reviews, 78(4), pp. 1165-1191. https://doi.org/10.1152/physrev.1998.78.4.1165 (Year: 1998).*
Homan et al. 2016. "Bioprinting of 3D Convoluted Renal Proximal Tubules on Perfusable Chips". Sci Rep 6, 34845. 13 pages total, https://doi.org/10.1038/srep34845 (Year: 2016).*
Jiménez-Torres et al. 2016. "LumeNEXT: a practical method to pattern luminal structures in ECM gels". Advanced healthcare materials, 5(2), p. 198-204; doi: 10.1002/adhm.201500608 (Year: 2020).*
Rein et al. 2020. "Effect of luminal flow on doming of mpkCCD cells in a 3D perfusable kidney cortical collecting duct model". American Journal of Physiology-Cell Physiology, 319(1), pp. C136-C147 (Year: 2020).*
Koslowski et al.; "An Overview of In Vivo and In Vitro Models for Autosomal Dominant Polycystic Kidney Disease: A Journey from 3D-Cysts to Mini Pigs"; whitepaper; Int. J. Mol. Sci. 2020, 21(12), 4537; Published Jun. 25, 2020; 34 pages; doi:10.3390/ijms21124537.
Sharma et al.; "In vitro cyst formation of ADPKD cells, Chapter 5"; Book; Methods in Cell Biology; vol. 153, pp. 93-111, 2019; doi: 10.1016/bs.mcb.2019.05.008.
Belmonte et al.; "Virtual-tissue computer simulations define the roles of cell adhesion and proliferations in the onset of kidney cystic disease"; Mol Biol Cell; 27(22); Nov. 7, 2016; 13 pages.
Bielmeier C, Alt S, Weichselberger V, et al.; "Interface Contractility between Differently Fated Cells Drives Cell Elimination and Cyst Formation"; Current Biology; 2016; 26(5): pp. 563-574; doi: 10.1016/j.cub.2015.12.063.
Sun, Y. et al.; "Drug discovery for polycystic kidney disease"; Acta Pharmacol Sin 32; 12 pages; Jun. 3, 2011; doi: 10.1038/aps.2011.29.
Liu B et al.; "Increasing extracellular matrix collagen level and MMP activity induces cyst development in polycystic kidney disease"; BMC Nephrol; 13:109; Published Sep. 11, 2012; doi:10.1186/1471-2369-13-109.
Mangoo-Karim, R. et al.; "Renal epithelial cyst formation and enlargement in vitro: Dependence on cAMP"; Proc. Nat. Acad. Sci USA; vol. 86. pp. 6007-6011; Aug. 1989. Physiological Sciences.
Zanetti F.; "Organ-on-a-chip, Engineered Microenvironments for Safety and Efficacy Testing, Chapter 7"; 2020; pp. 233-253; ISBN: 978-0-12-817202-5, doi: 10.1016/C2018-0-01892-7.
Schutgens, F., et al.; "Tubuloids derived from human adult kidney and urine for personalized disease modeling"; Nature Biotechnology, vol. 37, 2019; pp. 303-331; DOI:10.1038/s41587-019-0048-8.
Homan Ka et al. "Flow-enhanced vascularization and maturation of kidney organoids in vitro"; Nat Methods; Mar. 16, 2019; 16(3): pp. 255-262; doi:10.1038/s41592-019-0325-y.

(Continued)

*Primary Examiner* — Aaron J Kosar
*Assistant Examiner* — Andrew T Moehlman
(74) *Attorney, Agent, or Firm* — MASCHOFF BRENNAN

(57) ABSTRACT

A renal tube assay device can include: a container having an inlet port and an outlet port; a matrix material in the container; and a lumen in the matrix material extending from the inlet port to the outlet port. The lumen can include a luminal surface with at least one low density region that has a lower density compared to another adjacent region of the matrix material that is located at least partially around the at least one low density region. The low density region can have a form of a bubble, bulge, capsule, or the like. The low density region can bulge into the lumen. A port can be adapted for receiving a pipette tip. The matrix material can include a hydrogel. The container can be located in a cell culture dish.

20 Claims, 13 Drawing Sheets

(56) References Cited

OTHER PUBLICATIONS

Lin, Neil Y. C. et al.; "Renal reabsorption in 3D vascularized proximal tubule models"; Proceedings of the National Academy of Sciences; Mar. 2019; 116 (12); pp. 5399-5404; DOI: 10.1073/pnas.1815208116.
Lee et al.; "Kidney-on-a-Chip: A New Technology for Predicting Drug Efficacy, Interactions, and Drug-Induced Nephrotoxicity"; Current Drug Metabolism, 2018, 19, pp. 577-583; Accepted Nov. 12, 2017; doi: 10.2174/1389200219666180309101844.
Cruz Nelly M et al.; "Organoid cystogenesis reveals a critical role of microenvironment in human polycystic kidney disease"; Nat Mater.; Nov. 2017 ;16(11): pp. 1112-1119; doi: 10.1038/nmat4994.
Weber EJ et al.; "Development of a microphysiological model of human kidney proximal tubule function"; Kidney Int. 2016; 90(3); pp. 627-637; doi:10.1016/j.kint.2016.06.011.
Homan, K. et al.; "Bioprinting of 3D Convoluted Renal Proximal Tubules on Perfusable Chips"; Sci Rep 6, 34845; Oct. 11, 2016; 13 pages; https://doi.org/10.1038/srep34845.
Jang, K., & Suh, K.Y.; "A multi-layer microfluidic device for efficient culture and analysis of renal tubular cells"; Lab Chip; Jan. 7, 2021 10(1), pp. 36-42; doi 10.1039/b907515a.
Baudoin, Régis et al.; "Development of a Renal Microchip for In Vitro Distal Tubule Models"; Biotechnology progress. 23. pp. 1245-53. Doi:10.1021/bp0603513.
Rein et al.; "Effect of Luminal Flow on Doming of mpkCCD cells in a 3D perfusable kidney cortical collecting duct model"; Am J Physiol Cell Physiol 319:C136-C147; 2020; doi: 10.1152/ajpcell.00405.2019.
Chapron et al.; "An Improved Vascularized, Dual-Channel Mircophysiological system Facilities Modeling of Proximal Tubular Solute Secretion"; ACS Pharmacol Transl. Sci.; 2020; 2, pp. 496-508; doi: 10.1021/acsptsci.9b00078.
Cai et al.; "A RhoA-YAP-c-Myc signaling axis promotes the developments of polycystic kidney disease"; Genes Dev. Jun. 1, 2018;32(11-12):781-793. doi: 10.1101/gad.315127.118. Epub Jun. 11, 2018. PMID: 29891559; PMCID: PMC6049514.
Cordido A. et al.; "The Genetic and Cellular Basis of Autosomal Dominant Polycystic Kidney Disease—A Primier for Clinicians"; Front Pediatr. Dec. 18, 2017;5:279. doi: 10.3389/fped.2017.00279. PMID: 29326913; PMCID: PMC5741702.
Formica, C et al.; "Molecular pathways involved in injury repair and ADPKD progression"; Cell Signal. Aug. 2020; 72:109648; doi: 10.1016/j.cellsig.2020.109648; Epub Apr. 19, 2020; PMID: 32320858.
Miceli, C. et al.; The primary cilium and lipophagy translate mechanical forces to direct metabolic adaptation of kidney epithelial cells; Nat Cell Biol 22, 1091-1102 (2020). doi: 10.1038/s41556-020-0566-0.
Nigro, E. et al.; "Polycystin-1 Regulates Actomyosin Contraction and the Cellular Response to Extracellular Stiffness"; Sci Rep. Nov. 12, 2019;9(1):16640. doi: 10.1038/s41598-019-53061-0. PMID: 31719603; PMCID: PMC6851149.
Nigro, E. et al.; "Role of the polycystins as mechanosensors of extracellular stiffness"; Am J Physiol Renal Physiol. May 1, 2021;320(5):F693-F705. doi: 10.1152/ajprenal.00545.2020. Epub Feb. 22, 2021. PMID: 33615892.
Nishimura, R. et al.; "Solo and Keratin Filaments Regulate Epithelial Tubule Morphology"; Cell Struct Funct. Jun. 2, 2018;43(1):95-105. doi: 10.1247/csf.18010. Epub Apr. 28, 2018. PMID: 29709890.
Stoos, B. et al.; "Characterization of a mouse cortical collecting duct cell line"; Kidney Int. Jun. 1991;39(6):1168-75. doi: 10.1038/ki.1991.148. PMID: 1654478.

\* cited by examiner

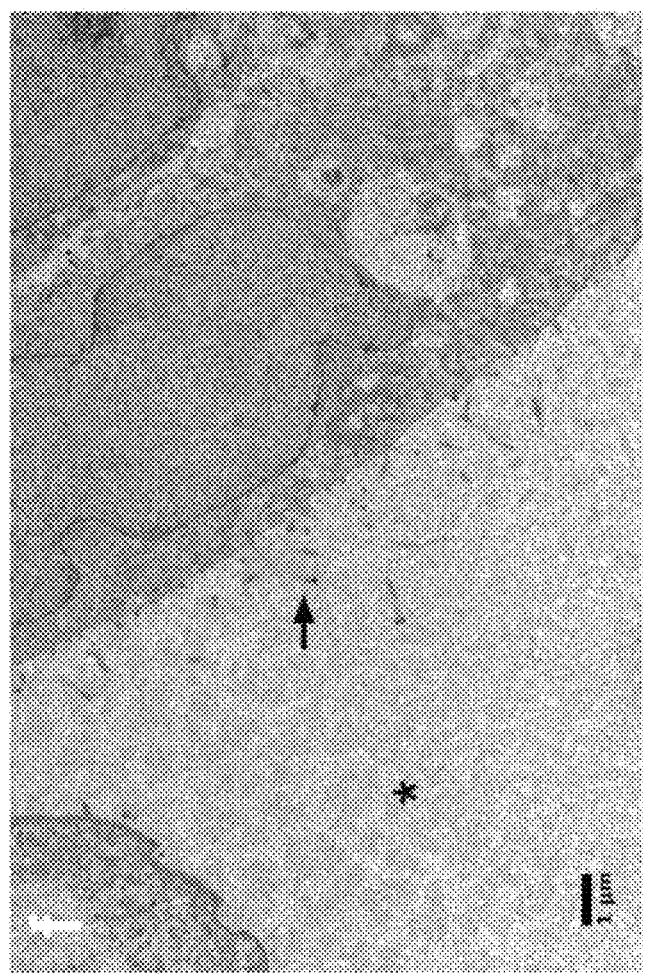
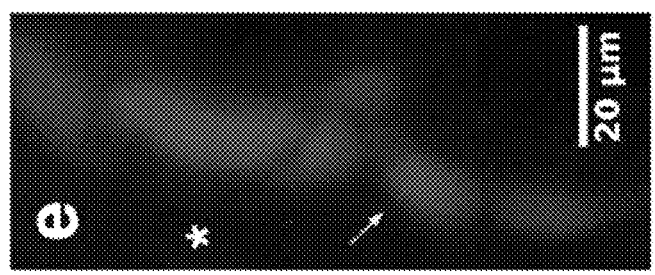
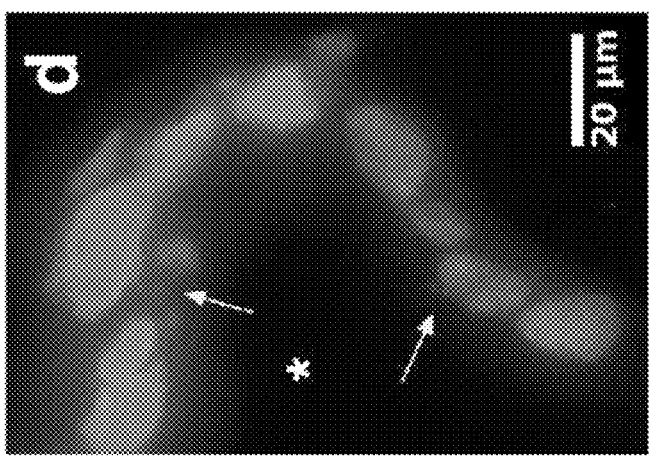
Fig. 2D
Fig. 2E
Fig. 2F

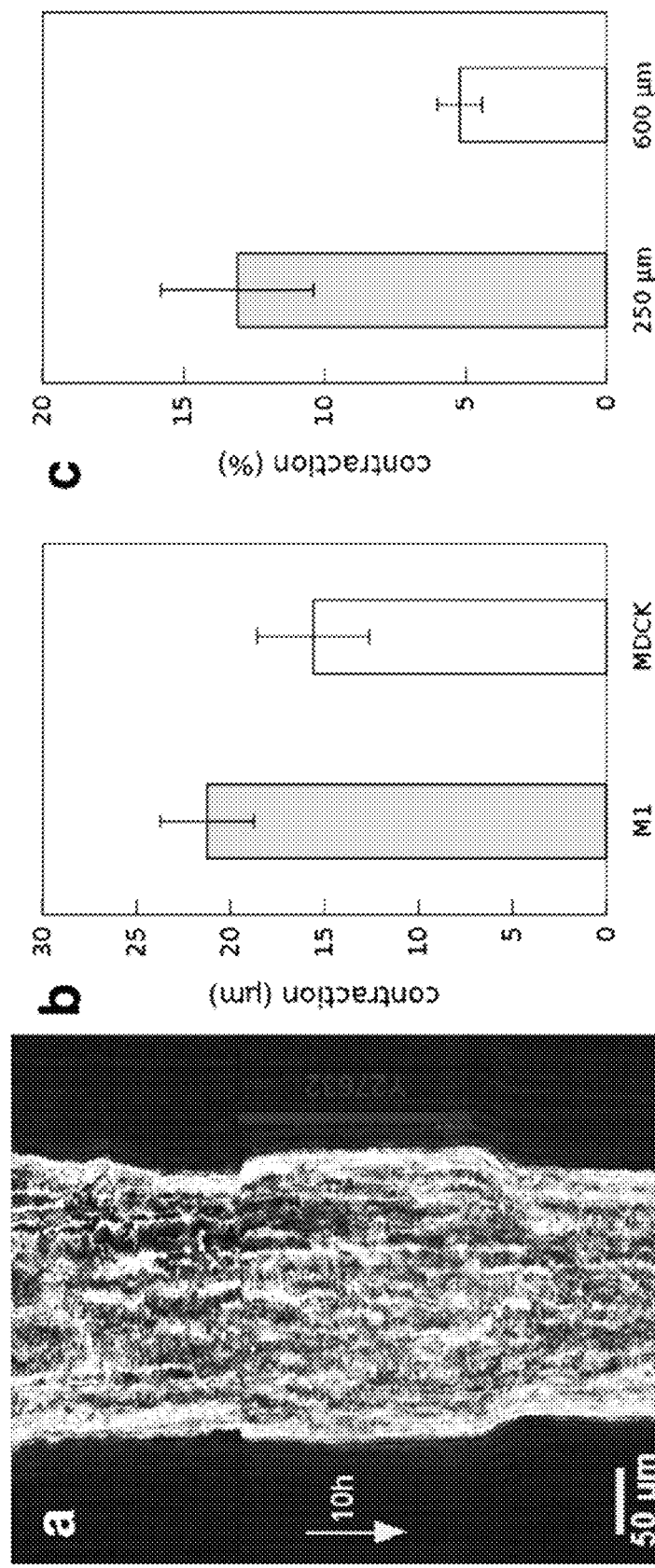

RENAL TUBE ASSAY DEVICE AND METHODS OF MANUFACTURE AND USE

CROSS-REFERENCE TO RELATED APPLICATIONS

This patent application claims priority to U.S. Provisional Application No. 63/109,630 filed Nov. 4, 2020, which provisional is incorporated herein by specific reference in its entirety.

GOVERNMENT SUPPORT

This invention was made with government support under DK106912 and DK103033 awarded by the National Institutes of Health. The government has certain rights in the invention.

BACKGROUND

Field

The present disclosure relates to systems and methods that utilize a renal tube assay device for studying the kidney and diseases thereof. The renal tube assay device can include features on simulated renal tubules for providing a physiological relevant model for studying the kidney and potential treatments for kidney diseases.

Description of Related Art

It is well known in animal physiology that the kidneys are vital organs that perform multiple functions, including blood filtration, osmoregulation, blood pressure and blood pH regulation, and Vitamin D activation. The kidney includes a large number of nephrons, each with a glomerulus that filters blood and forms a filtrate that passes through a kidney tubule that is lined with renal epithelial cells. These cells reabsorb and secrete nutrients, ions and wastes in a selective manner that modifies the intraluminal filtrate. The tubular lumen provides a flow that exerts hydrostatic pressure and shear stress at the apical surface of epithelial cells lining the renal tubule. Each cell is equipped with the appropriate cellular structure and molecular machinery to respond to the mechanical forces within the tissue microenvironment [1-4]. Other mechanical factors that impact a renal epithelial cell include stiffness of the underlying basement membrane, and connection to adjacent cells. It is known that faulty mechano-sensing results in an inadequate response to the mechanical factors in kidney diseases, such as autosomal dominant polycystic kidney disease (ADPKD), a genetic disease which causes progressive growth of fluid-filled renal cysts [5-7].

Previously, to improve the general knowledge of how complex tissue environments and mechanical factors contribute to renal tubule homeostasis and disease, several studies have proposed various in vitro models of kidney tubules. An epithelial monolayer within a flow chamber allows modulation of fluid flow [7]; however, these cells cannot undergo morphogenetic processes. Pluripotent or adult stem cells can be programmed to form a kidney with diverse cell types, but these organoid models cannot be readily subjected to hydrodynamic stress inside the developing tubules [8,9]. Also, organ-on-a-chip platforms allow formation of renal tubules to which intraluminal flow can be applied [10-13]. Therefore, there is a need for a kidney model that can be used to study kidney diseases (e.g., ADPKD) that mimics the tubule and morphological changes thereof.

SUMMARY

In some embodiments, a renal tube assay device can include: a container having an inlet port and an outlet port; a matrix material in the container; and a lumen in the matrix material extending from the inlet port to the outlet port. In some aspects, the lumen includes a luminal surface with at least one low density region that has a lower density compared to another adjacent region of the matrix material that is located at least partially around the at least one low density region. The at least one low density region can be a volume in the matrix material, where the low density region can be a void or a softer material that has a local density that is lower than another adjacent region or volume. For example, the matrix material can have a continuous region with one or more low density regions formed therein, which form as volumes of bubbles or lower density region compared to the continuous region. In some aspects, the at least one low density region has a form of a bubble, bulge, capsule, or the like. In some aspects, at least one port is adapted for receiving a pipette tip, such as the inlet or outlet port. In some aspects, the matrix material includes a hydrogel. In some aspects, the container is located in a cell culture dish. In some aspects, the low density region bulges into the lumen or opens into the lumen or is present at the surface of the lumen. At least one low density region can connect to the lumen. In some aspects, a cell culture (e.g., renal cells) is in the lumen, where the cells can grow in the lumen surface, which can line the lumen surface. The cells can also be in a low density region. The cell culture can be in at least one low density region, thereby forming a bulge structure. In some aspects, a renal cell culture is in the lumen with cells in at least one low density region, thereby forming a bulge structure.

In some embodiments, a renal tube assay system can include the renal tube assay device of any of the embodiments and a fluidic flow system comprising at least one pump fluidly coupled with at least one of the inlet port or outlet port. The at least one pump is coupled with a conduit that extends into a cell culture dish having the renal tube assay device in cell culture media. The system can include an analytical system operably coupled with the lumen in the matrix material. The analytical system can be an optical system having at least one optical device configured for acquiring images or video of the lumen. In some aspects, the system can include a rotational system having a rotational mechanism coupled to the container such that the container rotates with rotation of the rotational mechanism.

In some embodiments, a method of forming a bulge cell culture in a renal tube construct can include providing the renal assay system of one of the embodiments and culturing renal cells in the lumen and in at least one low density region to form a bulge in the matrix material with the renal cells. The method can include rotating the container and matrix material to rotate the lumen and renal cells therein during the culturing.

In some embodiments, a method of studying a bulge cell culture in a renal tube construct can include: providing the renal assay system of one of the embodiments; culturing renal cells in the lumen and at least one low density region to form a bulge in the matrix material with the renal cells; pumping a media fluid through the lumen; and monitoring the cells in the lumen and bulge. In some aspects, the monitoring is performed by optical monitoring with an optical system.

In some embodiments, a method of studying activity of an agent on a bulge cell culture in a renal tube construct can include: providing the renal assay system of one of the embodiments; culturing renal cells in the lumen and at least one low density region to form a bulge in the matrix material with the renal cells; pumping a media fluid containing the agent through the lumen; and monitoring the cells in the lumen and bulge.

In some embodiments, a method of forming a renal tube assay device can include: forming a container having an inlet port and an outlet port; forming a matrix material in the container around a lumen material, wherein the matrix material is formed to include at least one low density region that has a lower density compared to another adjacent region of the matrix material that is located at least partially around the at least one low density region; and withdrawing the lumen material to form a lumen in the matrix material extending from the inlet port to the outlet port, wherein the lumen includes a luminal surface with at least one of the low density regions. The method can include vortexing or bubbling a gas through the matrix material during formation of the matrix material (e.g., hydrogel). The method can include culturing renal cells in the lumen and at least one low density region to form a bulge in the matrix material with the renal cells. The method can include rotating the container and matrix material to rotate the lumen and renal cells therein.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE FIGURES

The foregoing and following information as well as other features of this disclosure will become more fully apparent from the following description and appended claims, taken in conjunction with the accompanying drawings. Understanding that these drawings depict only several embodiments in accordance with the disclosure and are, therefore, not to be considered limiting of its scope, the disclosure will be described with additional specificity and detail through use of the accompanying drawings.

FIGS. 2D-2E show the immunolocalization of primary cilia on M1 cells, with acetylated alpha-tubulin in FIG. 2D, Arl13B in FIG. 2E.

FIG. 2F shows a TEM image of M1 cells, with microvilli.

FIG. 3A includes a representative kymogram along a perpendicular cross section of a tubule of M1 cells in collagen I gel matrix, which is in response to a cell contractility inhibitor, Y27631.

FIG. 3B includes a graph of data that shows the contraction of tubules of M1 or MDCK cells, embedded in collagen I gels.

FIG. 3C includes a graph of data that shows the contraction of thin (250 µm) or wide (600 µm) tubules of M1 cells, expressed as percent of untreated tubule diameter.

Figure 1A:
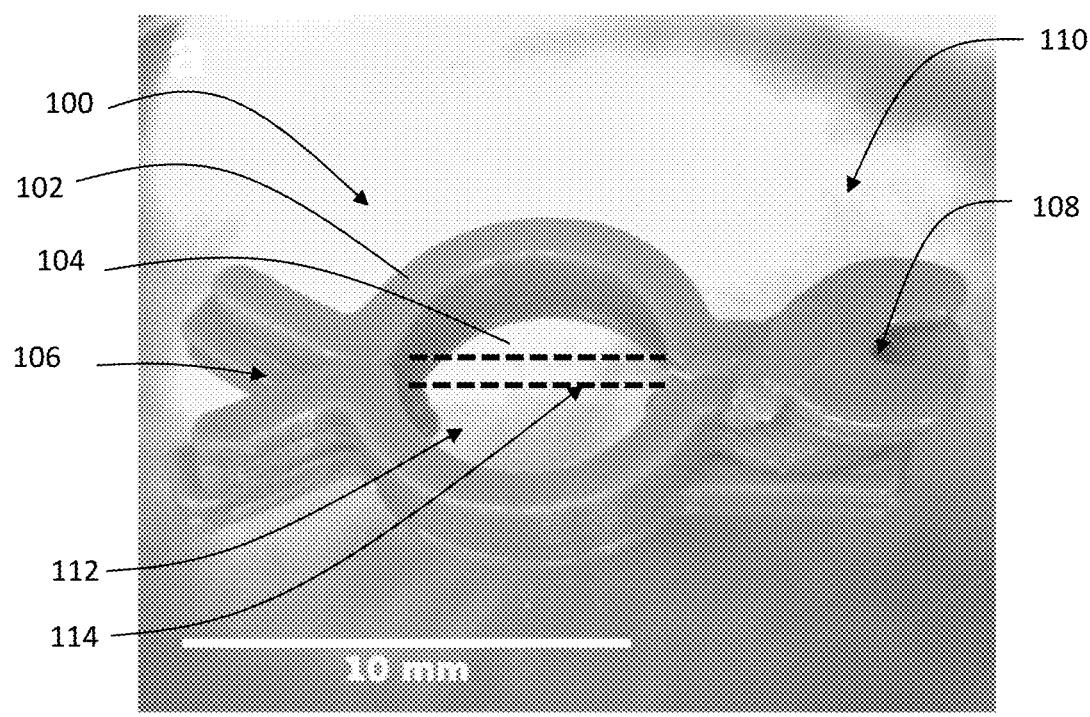
FIG. 1A includes an image that shows a flow chamber device in a cell culture dish.

The elements and components in the figures can be arranged in accordance with at least one of the embodiments described herein, and which arrangement may be modified in accordance with the disclosure provided herein by one of ordinary skill in the art.

DETAILED DESCRIPTION

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented herein. It will be readily understood that the aspects of the present disclosure, as generally described herein, and illustrated in the figures, can be arranged, substituted, combined, separated, and designed in a wide variety of different configurations, all of which are explicitly contemplated herein.

Generally, the present technology is related to systems and methods that utilize a renal tube assay device for studying the kidney and diseases thereof as well as treatments of the kidney diseases. The renal tube assay device can be configured to include a container having an inlet port and an outlet port with a test lumen therebetween for preparing cell cultures, such as those involved with the kidney and kidney cells. The device includes a hydrogel matrix in the container that is around the test lumen so as to define the lumen path. The hydrogel can include features that increase the ability to implement a cell culture and form kidney-simulating structures. The test lumen can be prepared as a tunnel in the hydrogel matrix extending from the inlet port to the outlet port, and can include the features for the cells to grow in and around to form cyst-simulating structures. The features are described herein, and can include regions of lower density hydrogel, bulges, bubbles, recesses, cavities, and other structures in the hydrogel for facilitating the cell culture with the kidney cells. The device can include renal cells (e.g., kidney epithelial cells) on a surface of the tunnel forming a renal tube. The cells can grow in and around the features to simulate different properties of a kidney, such as a kidney cyst, and can be used to study kidney diseases, such as polycystic kidney disease (PKD). The device can simulate a healthy or diseased kidney with the types of cells and the types of features (e.g., cavities, balloons, etc.) in the lumen walls.

FIGS. 1A-1D illustrate an example of a tubular flow chamber device 100 having a structure 102 with a round container arena 104 and two opposite ports 106, 108 that are in a cell culture dish 110. The container area 104 is filled with a hydrogel substance 112 surrounding a long and thin tunnel mask 114 that spans the container area 104 and connects the two ports 106, 108. The hydrogel 112 can be a type I collagen gel, a fibrin gel, or other combinations thereof.

The mechanical characteristics of the hydrogel 112 can be modified depending on the ECM protein type and concentration, as well as regions of inhomogeneity, bubbles, cavities, or other features. After removing the masking material 114, the hydrogel tunnel (114) is submerged in cell culture medium and seeded with renal epithelial cells 116 as shown in FIG. 1B.

Figure 1B:
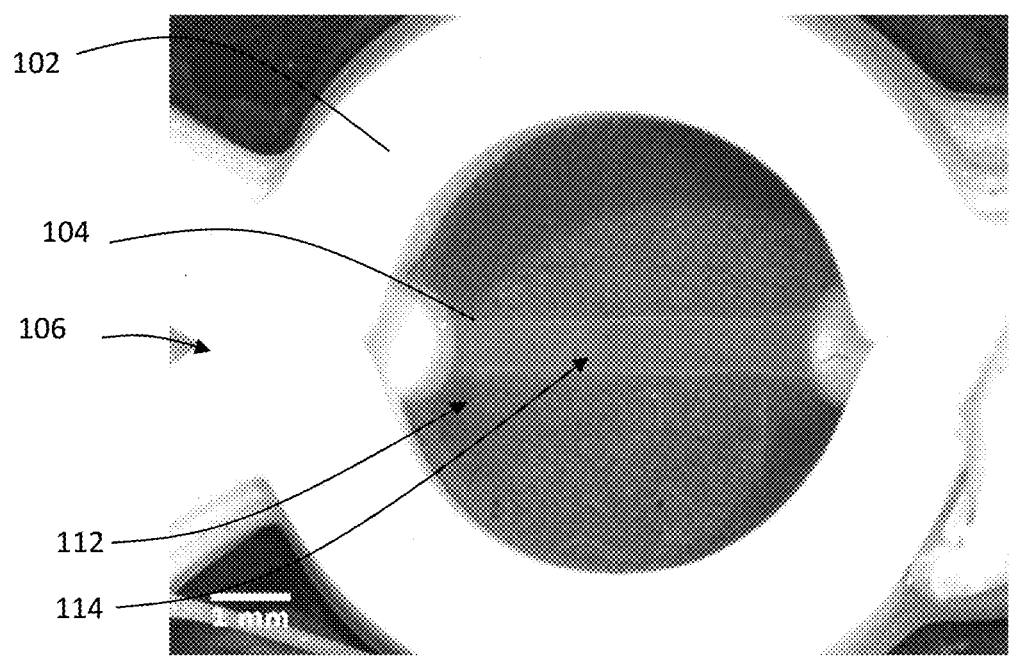
FIG. 1B includes an image that shows the flow chamber device having the hydrogel tunnel.
Figure 1C:
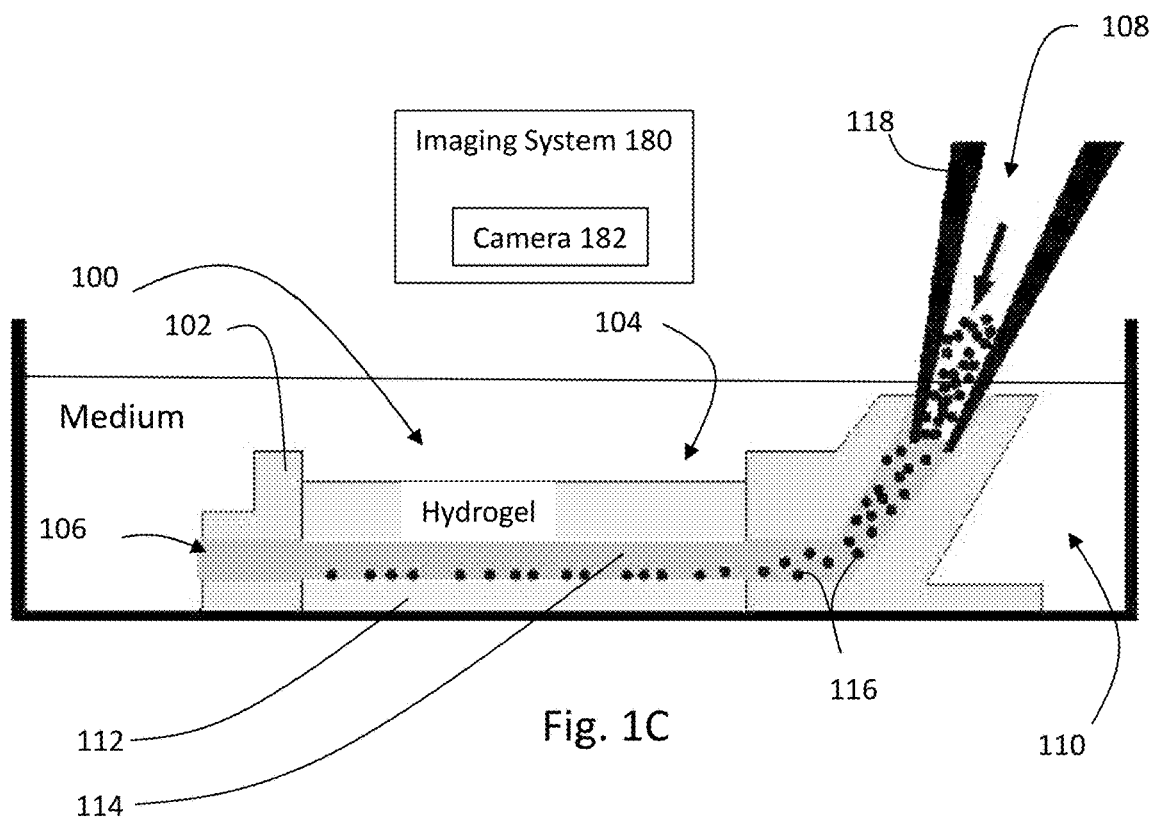
FIG. 1C includes a schematic diagram of cell seeding into the hydrogel tunnel of the flow chamber using a pipette tip at one of the ports.

As can be seen in FIG. 1C, an input device 118, which can range from a pipette, syringe, inlet conduit from pump system, or other input. The pipette input device 118 is inserted into the inlet port 108 to introduce cells 116 into the device 100 so as to go into the tunnel 114. Cells 116 can form a monolayer and the cell structures, such as bulges or cysts.

Figure 1D:
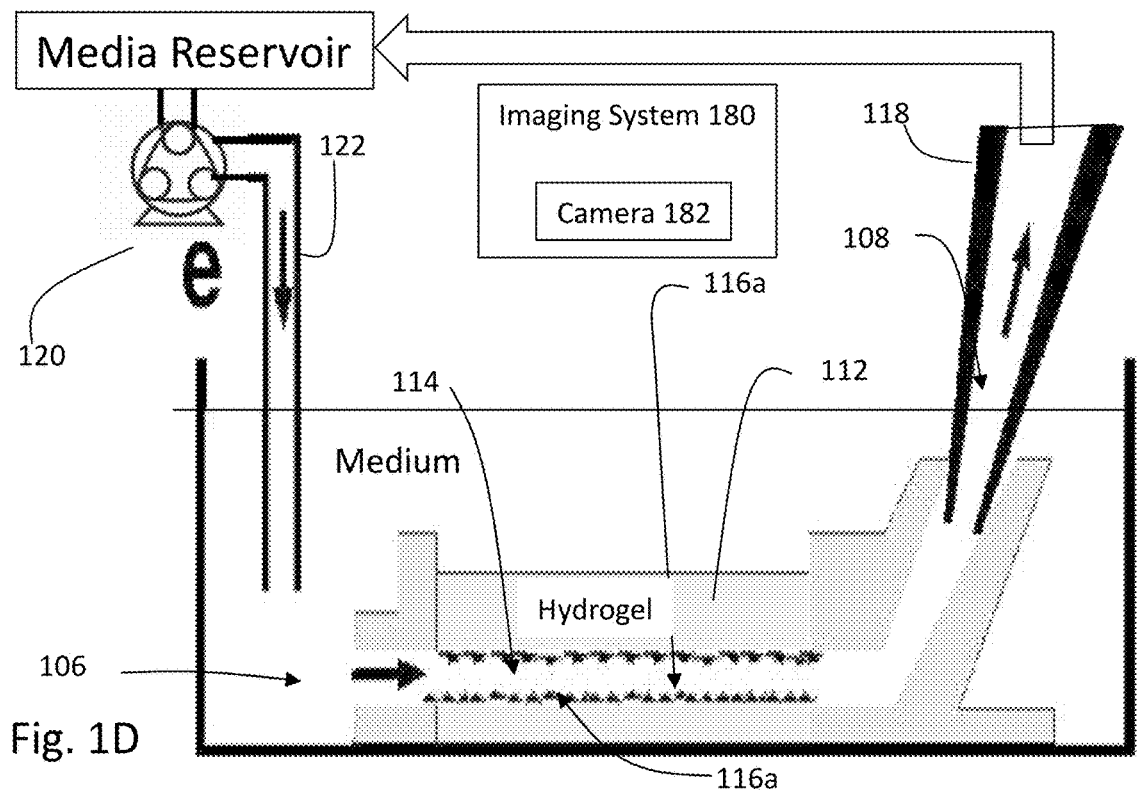
FIG. 1D includes a schematic diagram of a medium circulation system in the flow chamber device.
Figure 1E:
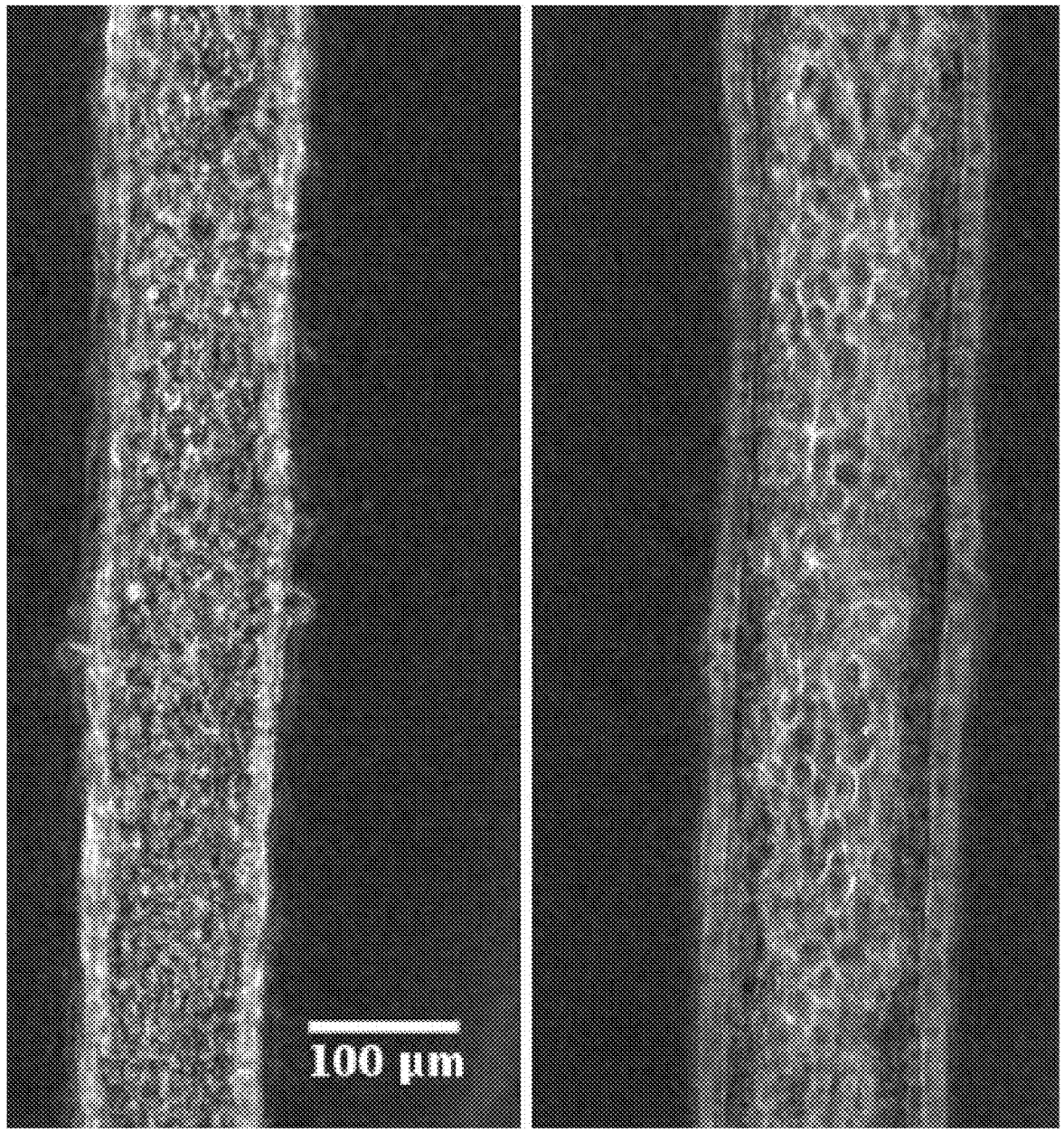
FIG. 1E includes an image that shows the hydrogel tunnel in the flow chamber with phase-contrast images of the bottom (left) and top (right) of a tunnel lined by M1 renal epithelial cells.

The structure 102 is kept under standard cell culture conditions, whereby epithelial cells (e.g., cells 116) migrate and proliferate within the tunnel 114, covering its surface as a cell monolayer 116a as shown in FIGS. 1D-1E. The device can be placed in a microscope stage cell culture incubator and subjected to live imaging, as shown in FIGS. 1C-1D. The morphology and motility of the cells 116, as well as changes in the size and shape of the renal tubule model lumen (e.g., tunnel 114) can be observed and recorded with live imaging microscopy for several days (FIG. 1D-1E). As such, imaging system 180 is positioned to image the tunnel 114 and cells 116 (e.g., cell culture monolayer 116a) with a camera 182, for still images or video imaging.

A peristaltic pump 120 pulls the medium from one of the ports (e.g., shown as outlet 116) via the conduit 122, and returns to the reservoir inside the culture dish 110. Thus, the flow of medium in the tunnel 114 of the renal tubule model is controlled by the rotational speed of a peristaltic pump 120. The flow path in FIG. 1D can be as shown or reversed.

The device can include various configurations, such as those described herein. For example, the hydrogel can form an elasto-plastic matrix with the features as described. In some aspects, the hydrogel is collagen, fibrin, or combinations thereof. The container can include 35 mm cell culture dish or other size, such as about 30-40 mm, about 25-45, about 20-50 mm, or smaller or larger as needed. The inlet port and outlet port can be fluidly coupled to at least one pump, such as a peristaltic pump, in order to provide the cells, media, test agents, and other components in an intraluminal fluid flow to the device or cells in the device. In some aspects, the cells in the container can be cultured in a way such that the renal cells form a monolayer with apical-basal polarity; however, other structures can be formed in addition to the monolayer, such as simulated cysts formed as bulges in the device. The renal cells, such as in the monolayer, can include laminin and fibronectin on a basal surface with primary cilia projecting from the apical sides of the renal cells into the tubular lumen of the renal tube. In some aspects, the features of the hydrogel in the device can be used to grow cells so as to form a bulge that simulates a cyst.

Figure 5A:
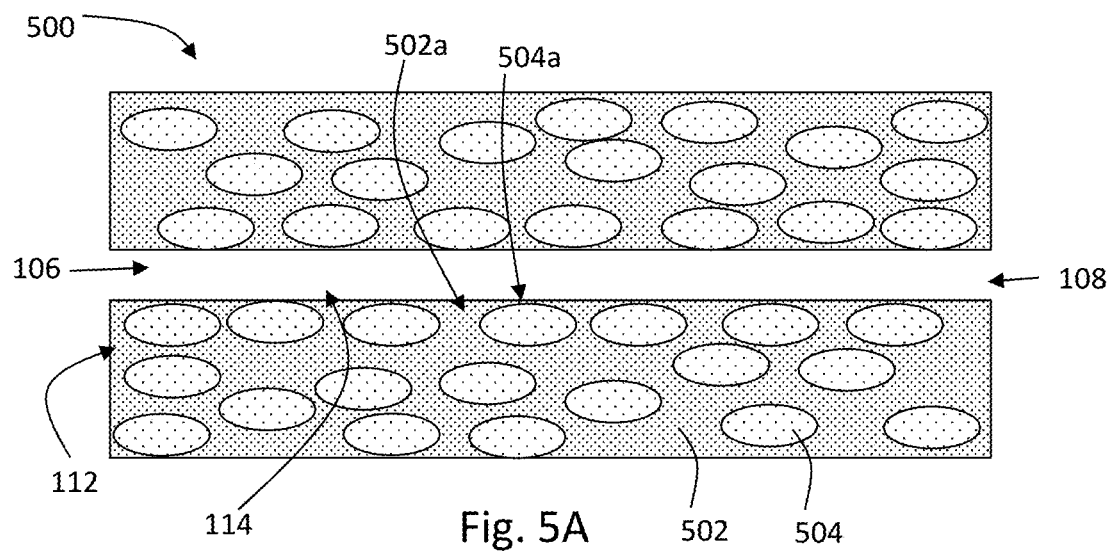
FIG. 5A illustrates an example of a renal tube assay device having a matrix material with regions of low density adjacent to an adjacent region with higher density than the region of low density, where the regions can be volumes in the matrix material, which can include sub-volumes.
Figure 5B:
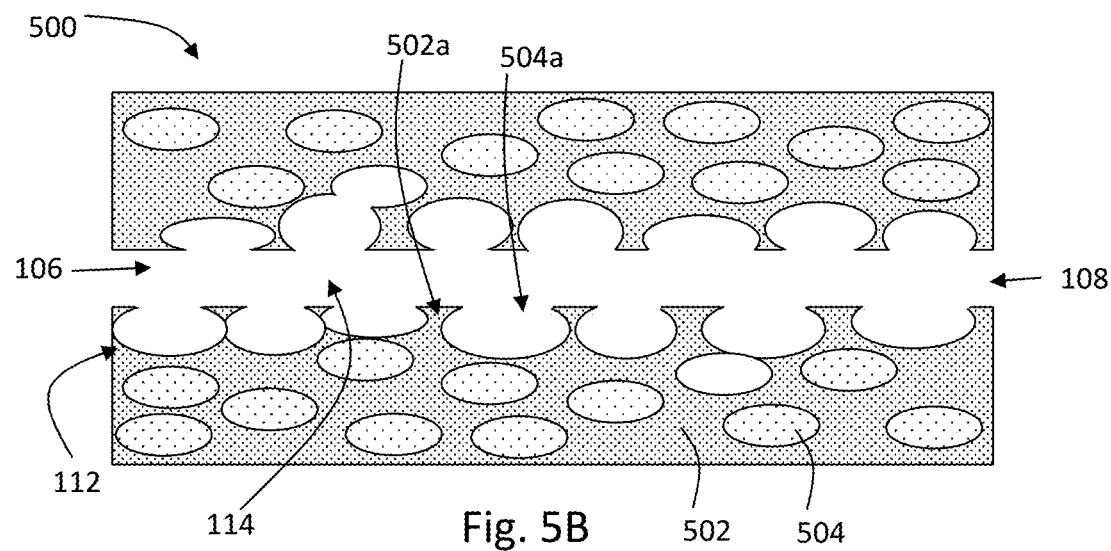
FIG. 5B shows the surface low density regions being in an expanded state so as to form a bulge, shown without cells.
Figure 5C:
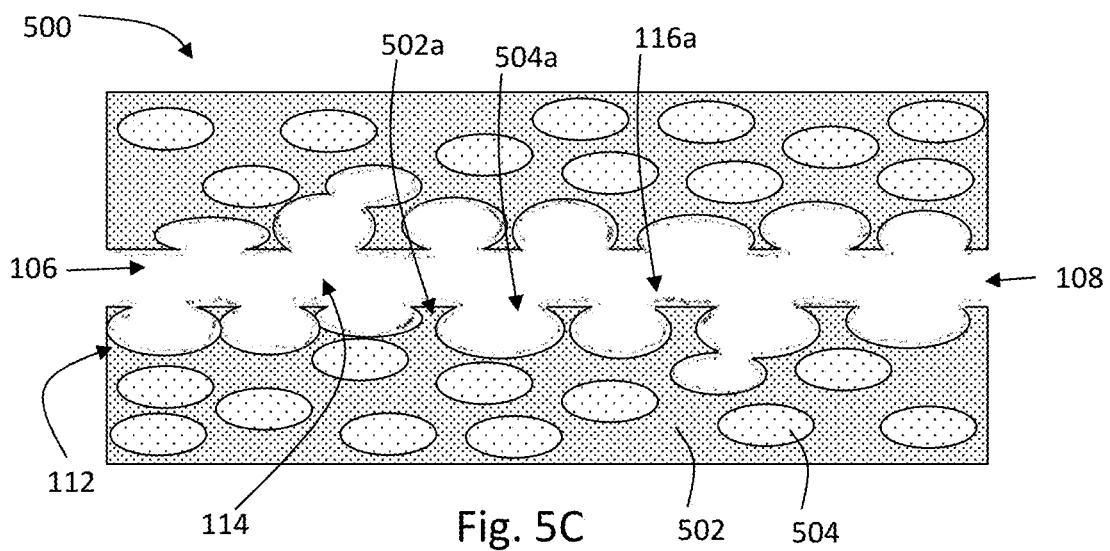
FIG. 5C shows the surface low density regions being in an expanded state so as to form a bulge containing cells.

FIG. 5A illustrates an example of a renal tube assay device 500 having a matrix material 112 with regions of low density 504 adjacent to an adjacent region 502 (e.g., higher density than the region of low density 504) of the regular matrix material (e.g., of the density of the continuous phase of matrix material). As shown, the inlet 108 and outlet 106 of the tunnel 114 are provided. The tunnel 114 can include surface low density regions 504a adjacent to the adjacent region 502a (e.g., of higher density, such as at least 4 mPa). FIG. 5A shows the surface low density regions 504a being in an initial state with a first lower volume, such as when without cells. FIG. 5B shows the surface low density regions 504a being in an expanded state so as to form a bulge, which can occur when containing cells; however, the device is shown without cells so that the structure of the matrix having the features (e.g., bubble, bulge) can be observed. FIG. 5C shows the device of FIG. 5B having the low density regions 504a having the cell culture forming a monolayer along the tunnel 114 and in the low density regions 504a.

Figure 5D:
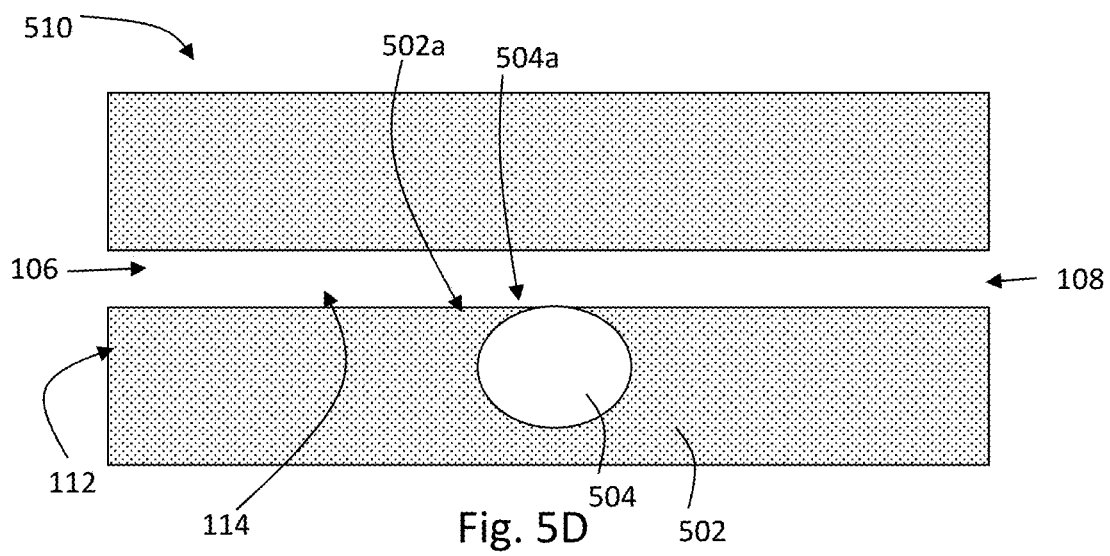
FIG. 5D shows a renal tube assay device with a single low density region in the adjacent region of the matrix.
Figure 5E:
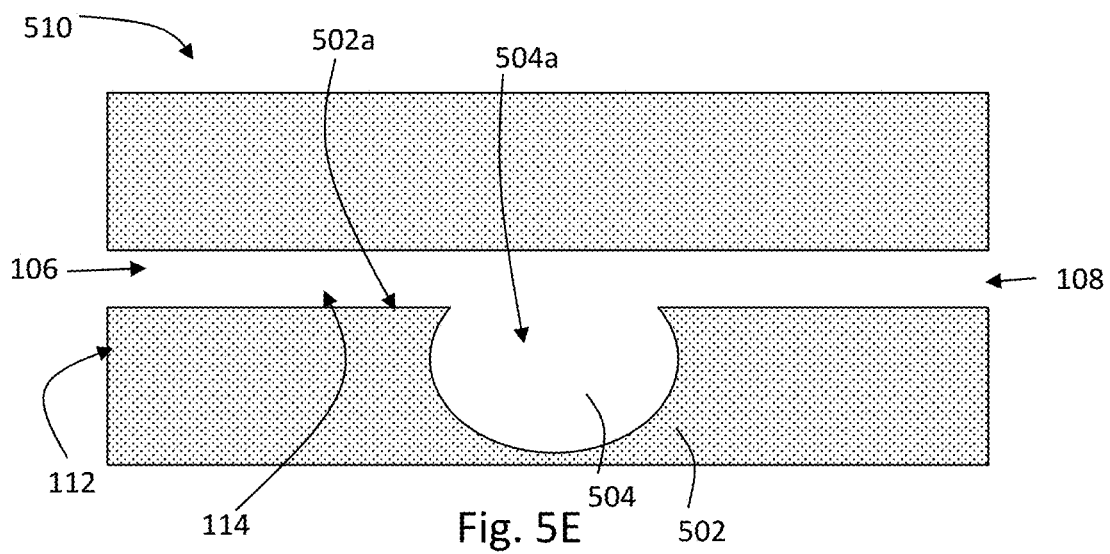
FIG. 5E shows the single low density region expanded in volume and extending into the tunnel, shown without cells.
Figure 5F:
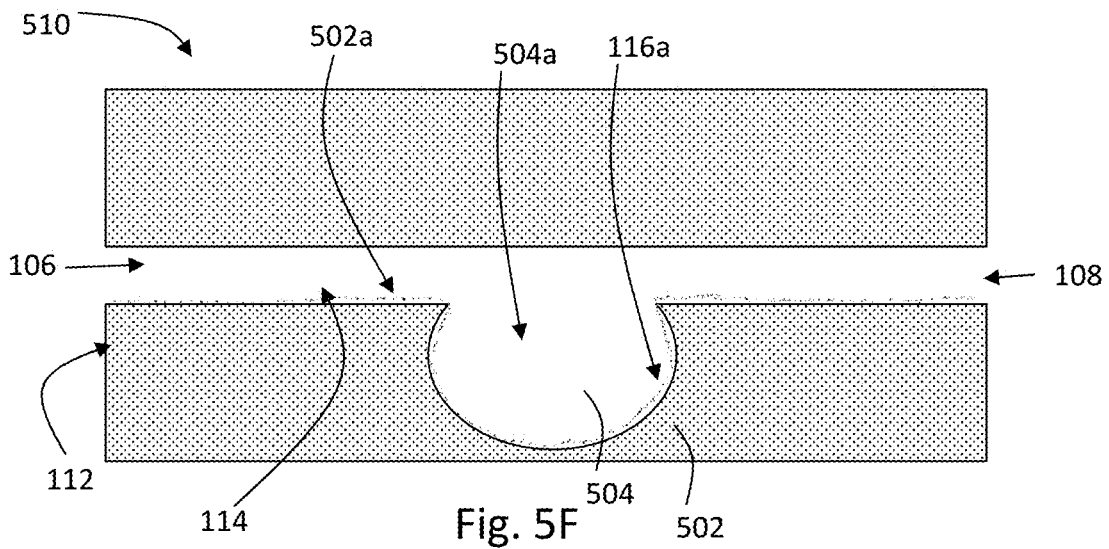
FIG. 5F shows the single low density region expanded in volume and extending into the tunnel, shown with bulge containing cells.

FIG. 5D shows a renal tube assay device 500 with a single low density region 504 in the adjacent region 502 of the matrix. Accordingly, any number of low density regions 504 can be included in the matrix material 112, as long as at least one is available. Also, the volume of the low density region can be varied. The adjacent region 502 can be the matrix material, which forms a majority of the solid volume. Gasses, bubbles, or low density matrix materials can form the low density regions. FIG. 5E shows the single low density region 504 expanded in volume and extending into the tunnel 114, which can be obtained when containing cells; however, the device is shown without cells so that the structure of the matrix having the features (e.g., bubble, bulge) can be observed. The structure can simulate a cyst, such as of a polycystic kidney. FIG. 5C shows the device of FIG. 5B having the low density regions 504a having the cell culture forming a monolayer along the tunnel 114 and in the low density regions 504a. FIG. 5F shows the device of FIG.

5E having the low density region 504 having the cell culture forming a monolayer along the tunnel 114 and in the low density regions 504a.

Figure 6A:
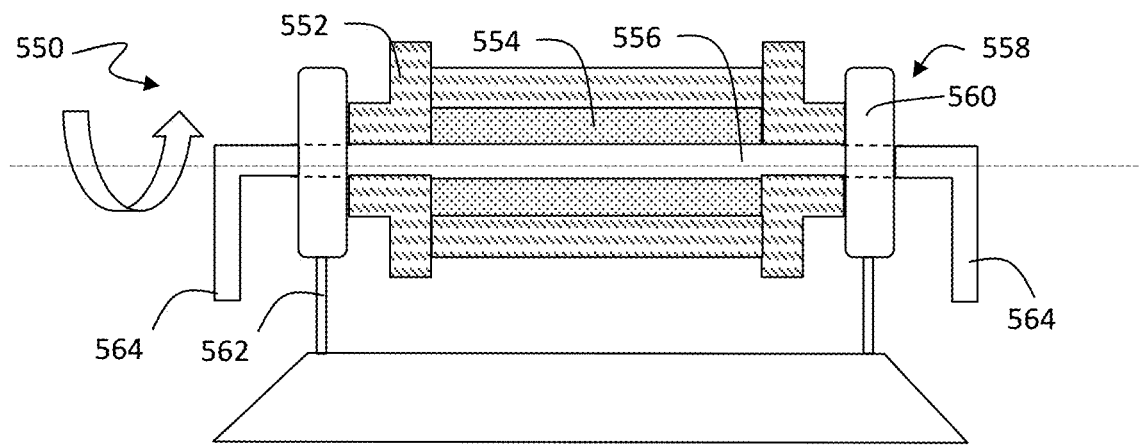
FIG. 6A shows a rotational renal tube assay device that includes the container having the matrix material with the lumen therein.
Figure 6B:
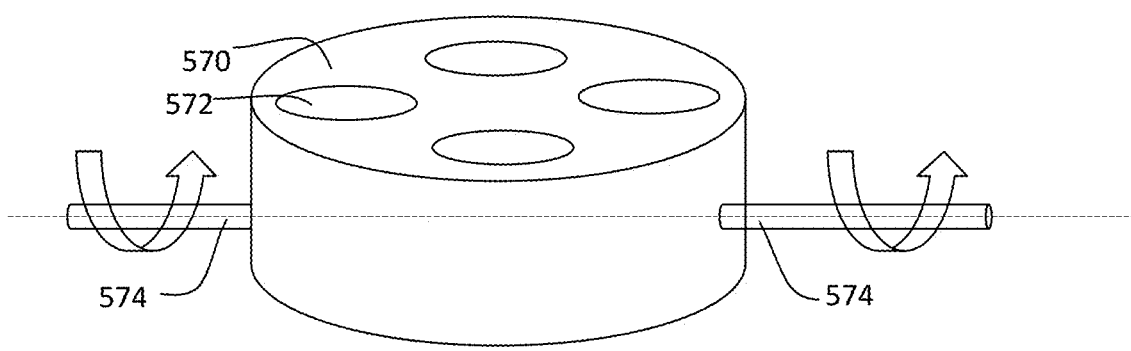
FIG. 6B shows the housing having air ports formed therein and configured for rotation.
Figure 6C:
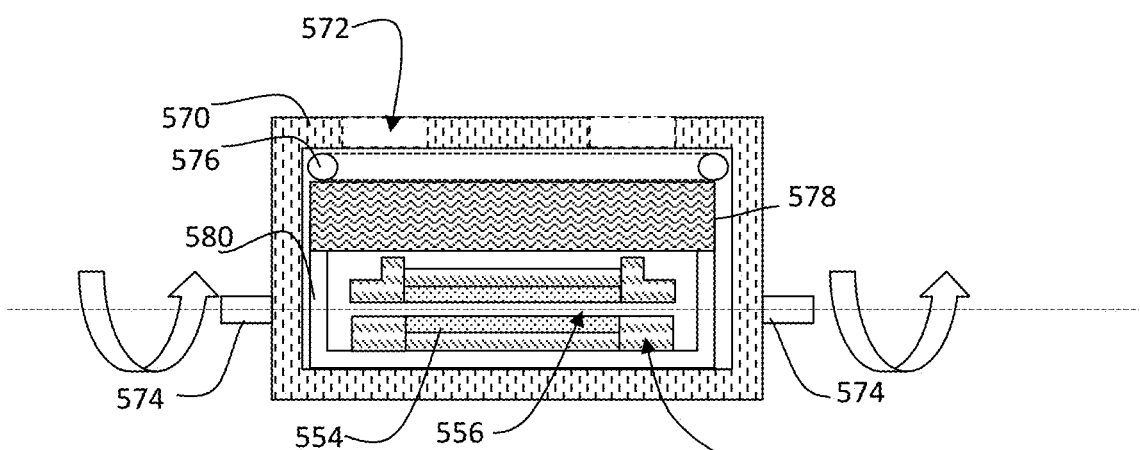
FIG. 6C shows a cross-sectional view of the device of FIG. 6B.

FIGS. 6A-6C illustrate different embodiments of renal tube assay devices that are configured with a rotating mechanism. The renal tube assay devices of the figures can be included in a cell culture container that can be rotated, thereby forming rotational renal tube assay devices. The rotational renal tube assay devices include a rotational mechanism that rotates the cell culture chamber having the cell culture in the lumen of the tube. The rotation of the cell culture in the lumen of the tube causes the cells to form a monolayer along the entire luminal wall. The rotation can cause the cells to form a substantially uniform monolayer along a circumference of the luminal wall. The rotation during cell culturing can also all for the cells to grow into the features in the luminal surface. For example, the cells can grow in the cavities or bubbles in the luminal wall, which can result in the cell-containing bulges. Each of the rotational renal tube assay devices can be outfitted with gas permeable (liquid impermeable) membranes to allow for gas exchange with the cell culture media. Thus, the cell culture can form a uniform monolayer from the onset of the culture. FIG. 6A shows an embodiment of a rotational renal tube assay device 550, which can be used for culturing cells along the luminal surface of the tube. FIG. 6A shows that the device 550 includes the container 552 having the matrix material 554 with the lumen 556 therein. The container 552 is coupled to a rotational mechanism 558, which can include a motor system 560 or other rotational device. The container 552 can be suspended with a support 562 to allow rotation along the axis shown by the dashed line and the rotation arrow. The ports 564 can be tubes that fluidly couple with the lumen 556, shown as dashed lines when going through the motor system 560. This device allows for rotation while culturing the cells so that the cells can form a monolayer on the internal surface of the lumen 556.

Accordingly, the device can be rotated while the cells are sedimenting, attaching, growing and while any assay is being performed. The device can also be set at a position and left in the position for a duration of time so that the cells culture on the bottom of this position, which position can be changed by rotation. While not shown, the gas permeable membrane can be included with the device to allow for gas exchange.

FIG. 6B shows the housing 570 having air ports 572 formed therein and configured for rotation. The housing 570 includes a rotational shaft 574 that can be coupled to a rotational mechanism, such as a motor system for rotation. The housing 570 can include the renal tube assay device located therein. FIG. 6C shows a cross-sectional view of the device, with the housing 570 containing an O-ring 576, which holds a gas permeable membrane 578 (e.g., liquid impermeable) as a cover for a container 580 (e.g., cell culture well, petri dish) that contains the renal tube assay device. There can be a gap between the housing 570 and the container 580 as shown, or it can be a tight fit. A renal tube assay device 580 is located in the chamber so that the lumen 556 is aligned with the rotational axis shown by the dashed line, where the rotation is shown by the arrow. The renal tube assay device 580 includes the matrix material 554 with the lumen 556 therein. This device allows for rotation while culturing the cells so that the cells can form a monolayer on the internal surface of the lumen 556.

In some embodiments, a method can be performed for forming a renal tube assay device, such as the device with the features described herein. The method can include obtaining a container having an inlet port and an outlet port. An elongated member shaped as a desired tunnel shape (e.g., pin, needle, shaft, whether straight, curved, etc.) is inserted between the inlet port and outlet port. A hydrogel can be prepared and introduced into the container around the elongated member in order to form a test lumen one the elongated member is withdrawn. The hydrogel can be configured with the features, such as regions of lower density hydrogel, bubbles, recesses, and other structures in the hydrogel for facilitating the cell culture with the kidney cells. The elongated member can be withdrawn from the hydrogel to form a tunnel between the inlet port and outlet port. Once the structure is set, renal cells can be introduced into the inlet port and then into the tunnel of the test lumen. The cells can grow on the surface of the test lumen and can associate with the features. The features can allow for the cells to grow into the features, which can then form the kidney structures, such as bulges or cysts, for studying with test agents.

The hydrogel can be prepared to form an elasto-plastic matrix with the features. While any hydrogel casting or forming operation can be used, the method can also include 3D printing the container onto a cell culture dish and optionally selectively 3D printing the hydrogel material so as to form the features. In some aspects, the inlet port and outlet port can be formed by 3D printing to form apertures or the ports are drilled into the body of the container.

Once the device is formed, a test system can be prepared by fluidly coupling the inlet port and/or the outlet port to at least one pump, such as a peristaltic pump. The pump can include a port to allow introduction of substances into the test lumen, such as cells, cell media, test agents, various fluids and gasses as known in the art of cell cultures. The renal cells can be introduced into the test lumen and cultured sufficiently to form a monolayer with apical-basal polarity. In some aspects, the cell culture can be performed in a manner for forming a renal cell monolayer that has laminin and fibronectin on a basal surface with primary cilia projecting from the apical sides of the renal cells into the tubular lumen of the renal tube.

In some embodiments, a method of studying renal cells can be performed with the device. The method can include providing the renal tube assay device and culturing appropriate renal cells. Preferably, the renal cells form structures, such as bulges or cysts, for observation and study. The various biological profiles of the cells and any biomarkers can be measured for analysis purposes. Any cell culture study to analyze the cells can be performed with the device.

In some embodiments, a method of studying a stimulus on cell in the renal tube assay device can be performed. Such a method can include providing a renal tube assay device having the features in the test lumen as described. Once the cells are sufficiently grown or cultured, a test method can include introducing a stimulus to the renal cells. The stimulus can be any change in the conditions of the cells, from oxygen percent, carbon dioxide percent, other gasses, temperature modulations, flow rate modulations, media modulations, nutrient modulations, and other stimuli can be applied. The stimuli can be a chemical, such as a potential drug, that can be tested on the state of the renal cells. The reaction of the renal cells to the stimulus, such as the drug, can then be observed and recorded. The reaction or other response by the cells can provide an indication as to how the stimulus changed the cells or modified the cell culture or structures thereof. In some aspects, the stimulus is physical, electrical, optical, and chemical (e.g., test drugs to treat PKD). In some aspects, the cell can be grown in the device to provide a renal tube model, which model can be configured with bulges or cyst structures to simulate polycystic kidney disease (PKD). In an example, the renal tube can be cultured to include MDCK renal epithelial cells, MI mouse cortical collecting duct cells, cell lines with genetic modifications to introduce PKD-associated mutations, and primary renal epithelial cells derived from normal human kidney and from PKD patients. In some aspects, the renal tube assay device can be cultured in a way so that the test lumen includes fluid-filled renal cysts, which may bulge into the lumen. During the studies with the device and renal cells, various types of assays can be used to determine any status or change in the cells and functionality in the device, whether or not associated with a stimulus. The assays can include chemical analysis of the media, which can include metabolites and other substances from the renal cells. Also, the assays can include visual analysis of the structure of the cell culture and morphologies thereof. For example, the assays can include imaging the renal cells through the renal tube assay device, which is transparent, such as the container and hydrogel being transparent. This allows an imaging device to image the cells in their condition within the device without removing the calls. Additionally, the analysis of the media obtained from the outlet can be indicative of the chemical and biological processes of the cells. Thus, multiple modes of analysis can be performed to provide an enhanced understanding of the renal cells and response to any stimulus provided thereto.

Accordingly, the configuration of the device, which allows for visual analysis, provides a versatile in vitro model system that can be used to study pathophysiology of kidney diseases and identify therapeutic compounds for these diseases. The in vitro system includes the tissue engineered renal tubule within an elasto-plastic extracellular matrix microenvironment. The tubule and the extracellular matrix microenvironment is within the container of the device with an inlet port and an outlet port. These ports can be configured as pipette-accessible ports to allow selective pipetting into the inlet, and selective pipetting from the outlet, which can be used for analysis of the media and components thereof. In some aspects, the container of the device can be included in a cell culture system, such as a filament-deposition (e.g., 3D-printed) into a cell culture device (e.g., 35 mm cell culture dishes).

The container of the device is filled with a hydrogel, such as a collagen I or fibrin gel as well as others, while a narrow masking tube (e.g., needle) is threaded through the ports in order to form the test lumen. Following gelation, the masking material is pulled out of the hydrogel and container, thereby leaving a tunnel within the gel. The device can be operable within a cell culture system, so that the cells can be properly cultured. The preparation of the cell cultures can begin with seeding of the tunnels with cells (e.g., renal epithelial cells) through the inlet ports and the cells can be cultured so as to obtain a monolayer with apical-basal polarity, such that laminin and fibronectin are present on the basal surface, while primary cilia project from the apical side of cells into the tubular lumen. The device is transparent so as to be optically accessible for visual analysis (e.g., with camera of imaging system), and can be live-imaged by phase contrast or epifluorescence microscopy or other visual analysis, such as any relevant images or videos.

In some experimental configurations, the test lumen of the epithelial-lined tube within the hydrogel can be connected through the inlet and outlet ports to a circulatory flow system, which can be driven by a peristaltic pump or other type of pump. Renal epithelial cells are able to adjust the tube inner lumen diameter by myosin-II dependent contractility, and are able to remodel the surrounding hydrogel environment and form cyst-like structures by infiltration into the low density regions. For example, this environment remodeling can be from the cells interacting and growing within an adjacent to the features in the hydrogel. A low density region or a bubble on the lumen surface can be suitable for enhanced cellular growth and culturing, and thereby expand the cell culture for developing bulges and cyst-simulating structures in the low density region or bubble.

The renal assay device allows for the implementation of various assays in order to study the role of mechano-sensing in kidney diseases, such as ADPKD, a genetic disease which causes progressive growth of fluid-filled renal cysts. In particular, the device allows the manipulation of tissue mechanical factors like apical fluid pressure, shear stress, basement membrane stiffness, tissue elasticity and contractility, as well as the evaluation of environment-induced cell responses. Furthermore, the device also enables the renal epithelial cells to modulate the mechanical state of the tissue environment, thereby creating a feedback regulation indicative of the physiology of the cells.

In some embodiments, renal cells are grown on the tunnel surface to form a renal tube. The renal tube can then be used in assays that test renal cells and renal tubes and responses thereof to different stimuli, such as physical, electrical, optical, and chemical (e.g., test drugs to treat PKD).

In some embodiments, the device is configured as a kidney tubule-mimetic device that allows systematic regulation of intraluminal flow and flow contents, as well as examination of various mechanical factors on the renal cells. The device is configured for a live in vitro culture system that is operably coupled to live cell imaging microscopy, which allows real time visualization of tubules that are contractile, renal cells remodeling the surrounding ECM environment, and the impact of various stimuli on the renal cells in the tubule-mimetic device.

In some embodiments, the device can be used to study an interaction between the genetic make-up, biochemical signals, and mechano-sensing of fluid shear stress and extracellular matrix (ECM) stiffness of renal epithelial cells along a cystic pathway. The device allows for controlled fluid flow in a kidney tubule mimetic. The device can be configured as an in vitro renal tubule model that allows manipulation of biological and biophysical factors. This can allow studying the renal tissue morphogenic events that culminate in a renal cyst. Such a system can be used for in vitro studies of PKD to identify mechanisms of the disease. The inlet port allows manipulation of genetic, chemical and mechanical factors and recapitulation of the tissue morphogenesis that results in renal cysts. To enhance data integrity and quality control, the system can use a continuous optical monitoring system that provides visuals of the simulated tubule and cell cultures. Also, the in vitro model can also be developed into a future pre-clinical screening tool to identify pharmacological compounds that will improve treatment of kidney diseases, such as ADPKD.

The device and implementation of assays can be configured to provide the correct combination of genetic, biochemical and mechanical conditions that prime a renal epithelial cell to become cystic. The mimetic device can be used with mouse, human, and patient PKD renal epithelial cells as well as others, and can provide various sources of biochemical signals to the cells in the hydrogel tunnel and low density regions (e.g., bulges). The tissue mechanical properties, primarily fluid shear stress, and ECM stiffness can modulate cyst formation.

In an example, the renal tubule mimetic can be a model for ADPKD drug discovery. This can include using the renal tubule mimetic to evaluate the effects of Tolvaptan or other drug in inhibiting the morphological events leading to cyst formation. The system can enable identification of essential and modifying factors of cyst formation, from which a hierarchy and interactive network of renal cyst drivers can be elucidated.

The cells in the device can be derived from M1 mouse cortical collecting duct cells; M1 (control) and M1 C20 (e.g., a PCI dominant negative mutant) cells; RCTE human cortical collecting duct cells; Pkdlmutant RCTE cells; and primary renal epithelial cells derived from normal human kidney (NHK) and ADPKD renal cortical collecting duct tissue. In some embodiments, the hydrogel can be configured for enhancing bulge or cyst formation. The hydrogel can be treated with 100 µM cAMP and 10 nM EGF, which induce cell proliferation and fluid secretion. The cells can be visually analyzed to show more dilations or out-pockets (e.g., simulated cysts) than WT cells. In some aspects, Matrigel, a tumor-derived ECM that is rich in laminin and collagen IV, can be added to the collagen I hydrogel. The Matrigel-collagen combination can be used for cyst formation of kidney epithelial cells grown in a scaffold-based culture on the lumen in the device. In some aspects, decellularized kidney ECM can be obtained and mixed with the hydrogel to provide biological relevance to the hydrogel, where homogenized decellularized ECM samples can be mixed with collagen I solution prior gelation.

In some embodiments, the imaging system can record changes in the morphology of renal tubules by optical microscopy. An analytical system, such as a computer (e.g., standard computer with processor, memory, etc.), can be used to examine for the presence of bulges (e.g., dilations/out-pocket protrusions) and cysts, which can also be done by human inspection. Multicellular rearrangements can be tracked by brightfield images. Analysis of optical recordings can be performed [23-29]. Also, immunofluorescence and electron microscopy can be used to evaluate cell proliferation, basement membrane ECM composition, renal polarity, differentiation (e.g., DBA, and cilia lengths), which are altered in PKD.

In some embodiments, data can be collected in order to compare dilation and cyst formation in the presence and absence of intraluminal flow, and with or without active agents. As the tubule diameter is in the ADPKD range (250 µm), the system can employ flows either with the physiological velocity of 1 mm/sec and a corresponding ADPKD shear stress of 0.01 Pa, or with a higher 10 mm/sec velocity with a wall shear stress in the physiological range at 0.1 Pa. The connection between wall shear stress and flow velocity can be calculated by the assumption of a laminar flow with parabolic velocity profile within a cylindrical tube. The system can be used to monitor changes in tubule shape as well as the corresponding cellular rearrangements, and changes in cilia length. It is expected that for normal kidney epithelium, a physiological shear stress is protective from cystogenesis, while a reduced luminal shear stress promotes cystogenesis. Additionally, since flow is absent in cysts, flow can be regulated and stopped for a period of time. This could include a mechanism that promotes in vitro expansion of cysts after the initial budding event.

In some embodiments, the hydrogel can be configured to have an increased stiffness by mixing collagen with components of an interpenetrating network (IPN) hydrogel composed of biologically inert components, agarose and poly (ethylene glycol) diacrylate (PEG-DA). The stiffness of IPN gels can be fine-tuned in the biologically relevant 1 kPa-100 kPa range. The mixture may not be homogenous, which allows for the regions of low density or bubbles.

In some embodiments, the protocols can include forming fluffy electrospun scaffolds. The physiological stiffness values can be varied so as to be protective for cyst initiation. Conversely, hydrogels can be formed with regions that are soft that enable renal cells to penetrate the low density region in the hydrogel, with the renal epithelial cells being able to form cysts.

In some embodiments, the conditions that enable cyst formation can be provided and the tubule mimetics of the device can be treated with tolvaptan to attenuate dilations/cysts formations. This can be used for validating the system as a platform to test pharmacological compounds, such as active agents as potential drugs. Also, tolvaptan can be used as a control to compare other potential drugs against.

In some embodiments, the hydrogel in the device can be configured to incorporate fibroblasts into the ECM, which can be used to examine whether additional signals are emitted by fibroblasts and to examine the interaction between renal epithelial cells and surrounding fibroblasts, well as the impact on response to active agents. In some aspects, if cysts are not observed, then the protocol can manipulate the cells genetically by lentiviral expression of Cadherin 8 (Cdh8). The device can then be cultured with a combination of PKD cells with and without Cdh8 overexpression, which can be used to determine whether cells that form out-pockets, bulges, or cysts overexpress Cdh8.

In some embodiments, the device can be used in a rotational system in order to generate uniform cell density within the tubule and to reduce the time needed for cells to establish a monolayer on the hydrogel tunnel surface. The rotational system can be used to rotate the cultures. Furthermore, to provide long-term stability of the hydrogel/ECM, the fluffy (foam-like) electrospun material scaffolds can be used within the hydrogel. The fluffy regions can be the low density regions that form the bulges or cyst mimic when infiltrated by the renal cells. This electrospun material can also be used to adjust the bulk material properties of the hydrogel environment.

Additionally, low density hydrogel or other low density gel materials can be mixed inhomogeneously though the hydrogel. For example, a lower density hydrogel can be formed and processed into smaller particles that can be around the size of a desired cyst, and then mixed into the hydrogel. These lower density regions can then preferentially be colonized to form bulges or cyst mimics. In some aspects, the electrospun material can be configured to be fluffy or lower density than the hydrogel, which allows the cells to penetrate into the low density region of the electrospun material. In some aspects, the electrospun material can be densely spun to be denser than the hydrogel, and thereby the hydrogel can be softer to allow cell migration and bulge/cyst formation therein instead of in the denser electrospun material. The stiffness of the low density region or less stiff region that allows cell penetration can be less than 4 kPa stiffness, such as less than 3 kPa, less than 2 kPa, less than 1 kPA, less than 500 Pa, and greater than 100 kPa or any range between these values.

In some embodiments, the cells are seeded into the hydrogel tunnel so that they sediment at the bottom surface. After attachment, cells proliferate and move to create a uniform monolayer throughout the entire hydrogel tunnel.

This process can take up to a week to complete. Furthermore, a cell density imbalance can occur between the bottom and top surfaces of the hydrogel tunnel. As such, the system can include a rotational system configured to rotate the culture chamber around the axis of the hydrogel tunnel during at least the cell sedimentation and attachment phase. In implementation, the culture dish can be filled with medium and covered with a lid with a sterile, gas-permeable polyurethane membrane. The membrane is pressed against the dish to make an airtight seal within the fabricated device, which has openings at the bottom and top surfaces to allow optical microscopy and gas exchange. The sealed unit containing the culture dish can then be enclosed in a tissue culture incubator and rotated with a stepper motor in a precisely controlled manner. After cell attachment is complete, the culture dish can be removed from the device, covered with a standard lid and standard tissue culturing protocols can be resumed. The plastic parts of the device can be 3D printed, and the controller electronics can be configured for rotational operation.

In some embodiments, the renal cells can be treated with forskolin or cAMP, which can be used to increase cell proliferation. This can allow for formation of cell structures in hollow, empty bubbles inside of the hydrogel. The compound can help form the cyst mimics in the device. The low density or soft regions can also help facilitate bulge growth and expansion with the renal cells. In some aspects, bubbles can be introduced into the gel during gelation to form the low density or soft regions for the cells to migrate and penetrate into. The bubbles can be introduced by blowing air into the gel during formation or by vortexing, as well as using lower density materials. The low density regions or bubbles allow for penetration and expansion so as to protrude into the tunnel in the hydrogel, which simulates a tubule cyst.

In some embodiments, the renal tubule mimetic structure can undergo contraction. The treatment of the cells with a direct or indirect myosin inhibitor, which is used as an inhibitor of contraction for expanding the tunnel, can be used to simulate expanding the tubule. Accordingly, studies without the myosin inhibitor can monitor contraction. Studies with the myosin inhibitor can monitor expansion. Removal of myosin inhibitors can then be used to induce more contraction. Some examples of myosin inhibitors can include blebbistatin, N-benzyl-p-toluene sulphonamide (BTS), 2,3-Butanedione monoxime (BDM), pentachloropseudilin (PCIP), pentabromopseudilin (PBP), MyoVin-1,2,4,6-Triiodophenol (TIP), or others. Some examples of indirect inhibitors of myosin activity can include the Rho kinase (ROCK) inhibitor Y27632 or DJ4. This protocol can be used for measuring contractability of renal cells, as well as any epithelial cell.

In some embodiments, the device can be used for a method of measuring contractile function of an epithelial tubule, such as a vascular tubule. This can include administration of the myosin inhibitor.

In some embodiments, the lumen of the device includes the port to the media reservoir in the cell culture device. The suction can pull the media from the reservoir into the device, such as the port 106 as in FIG. 1D. There can be suction at port 108 so that the media in the culture dish is drawn into port 106 and through the tunnel 114 and out the port 108. Thus, suction through the tunnel 114 into the media reservoir of the culture dish is used to draw media into the tunnel 114.

In some embodiments, port 106 and the circulation tubing 122 can form a closed system without connecting to the medium in the culture chamber. In such a configuration, a hydrostatic luminal pressure can be created if the epithelial monolayer is fully formed and acts as a barrier against fluid penetration.

In some embodiments, the renal tube assay device provides an in vitro model that allows analysis of kidney cell, structure, tubules, and different morphologies, such as bulge or cysts. The model can be used for improving the understanding of mechanisms underlying normal tissue development, homeostasis, and disease pathogenesis in the kidney. For example, in vitro models of ADPKD can be generated with the proper cells in the device described herein so that the bulges form to simulate cysts, which can be used for identifying molecular mechanisms and screening of pharmacological compounds. The device adds upon current in vitro kidney models including: an embryonic metanephric organ culture of mid-gestational kidneys isolated from mouse models [17, 18]; formation of in vitro microcysts using ADPKD patient-derived renal epithelial cells cultured in a collagen gel with growth factors [19], and programming of patient-derived induced pluripotent stem (iPS) cells into kidney organoids [20], by allowing for intraluminal fluid flow and pressure as well as renal epithelial tubular morphogenesis. Thus, these studies can be performed with the present device. While the embryonic metanephric organ culture and iPS-derived organoids model a developing kidney, the use of adult stem cells to generate kidney organoids and culturing of renal epithelial cells can be used to model the adult kidney and adult renal tubule, respectively [11, 21].

Due to the kidney having renal tubules through which filtrate passes, renal epithelial cells are subjected to intraluminal flow and pressure. In some aspects, the device can be configured to include in vitro renal tubules generated similar to a chip platform that allows for intraluminal flow [11-13]. The device can be used with an in vitro system that is coupled to an imaging system to perform live microscopy, which enables the renal epithelial cells to be viewed at any time point or as continuous and real time video.

The data provide herein demonstrates that renal epithelial cells seeded in the tunnel form a monolayer, with proper apical-basal polarity and formation of tight junctions between adjacent cells. Additionally, the in vitro renal tubule is able to dilate and contract within the extracellular matrix, in response to changes in Rho-associated coiled-coil-containing protein kinase (ROCK) signaling. Mechanical factors are an important component in regulating tissue development and homeostasis, and in turn, disease pathogenesis.

EXAMPLES

Materials and Methods
Cell Cultures

MDCK (Madin-Darby canine kidney) cells were purchased from ATCC and were cultured in DMEM medium (Lonza (2, 12-604F) supplemented with 10% FBS (Gibco®2). MI mouse renal cortical collecting duct epithelial cells were obtained from Dr James Calvet (University of Kansas Medical Center) and cultured in DMEM/F12 medium (Bio Sera, LM-D1223) supplemented with 10% FBS (Gibco §). All cultures were maintained in 6-well culture plates (Greiner) at 37° C. in a humidified incubator with 5% CO2 atmosphere. Once confluent, cell monolayers were washed in phosphate-buffered saline (PBS) twice, briefly incubated in trypsin-EDTA (Lonza®), then resuspended in their respective culture medium as a cell suspension. These suspensions were used to seed the tubule mimetic device.

Hydrogels

Type I collagen gels were prepared with 3.0 mg/ml collagen concentration (rat tail collagen I, Corning (2) according to the manufacturer's gel preparation protocol. Briefly, collagen I dissolved in 20 mM acetic acid (Corning &, 354236) was neutralized with 1M NaOH and 10×PBS (Lonza and transferred to 37° C. Gelation of collagen was completed in the mimetic device chamber in 30 minutes.

Fibrin gels with 3 mg/ml fibrin concentration were prepared as described earlier [15]. Briefly, 3 mg/ml human fibrinogen was combined with 200 U/ml aprotinin, 2 U/ml human thrombin, 2.5 mM CaCl2 (all from Sigma) and 2 U/ml human factor XIII (CSL Behring $) then the solution was transferred and allowed to gel in the flow chamber arena.

Flow Chamber Fabrication

Hydrogel chambers for the kidney tubule mimetic device were filament-deposition (3D-) printed using commercial polylactic acid (PLA, Verbatim) into 35 mm cell culture dishes (Greiner) as previously described [16]. The hydrogel chamber is an open round arena with 6 mm diameter and 50 µL volume. The lumen was created by threading either a teflon® tube of 500 µm outer diameter (Sailu Technology) or a damyl line of 250 µm diameter (Titan) through the opposite ports of the PLA structure-serving as masks for the tunnel spanning the hydrogel chamber. However, the diameter of the tunnel can vary from 100 µm diameter to 1,000 µm diameter, from 150 µm diameter to 750 µm diameter, from 175 µm diameter to 600 µm diameter, from 200 µm diameter to 500 µm diameter, 225 µm diameter to about 400 µm diameter, or about 250 µm diameter to about 300 µm diameter. After sterilization with 70% ethanol, the arena is filled with a hydrogel solution. After gelation the masking tube or line is removed leaving a 6 mm long void tunnel connecting the two open ports. The flow chamber is then filled up with cell culture medium and placed in the CO2 incubator at 37° C. for 2 hours to let the hydrogel equilibrate with medium. After equilibration, the tunnel is seeded with renal epithelial cells injected through either port as a dense cell suspension (10,000 cell/µL) readily prepared from a monolayer culture by washing up cells after brief incubation with trypsin-EDTA solution (Sigma). Cell attachment, proliferation and migration on the hydrogel tunnel wall eventually results in full lining of the entire surface of the tunnel by a monolayer of cells in 1 to 3 days under standard cell culture conditions.

Medium Circulation

Once a cell monolayer is established in the tunnels, the kidney tubule mimetic devices can be connected to circulation through the side ports of the hydrogel chamber. While culture medium covers the entire chamber in the culture dish, the circulatory flow of the culture medium through the tunnel is driven by a peristaltic pump (Ismatech, Mini-S 820) equipped with a cell culture grade peristaltic pump tube (Cole-Parmer $, Tygon E-3603, ID=1.4 mm). Teflon® tubing (Bola S1810-12) of 1 mm inner diameter was used to connect the pump and the devices within a microscope stage-top incubator. The typical flow rate of the pump was set to 0.66 µL/s.

Histology and Immunolabeling

For histology and immunolabeling, in vitro tubules were fixed with 4% paraformaldehyde in PBS. Some renal tubules were embedded in paraffin, and sectioned at 7 µm thicknesses using a microtome. For histology, sections were deparaffinized and rehydrated through a series of ethanol washes and finally stained with hematoxylin and eosin (H&E) or toluidine blue. For immunodetection of cilia, the renal tubule sections were deparaffinized, rehydrated, then subjected to antigen retrieval. Tissue sections were steamed for 15 minutes in sodium citrate buffer (10 mM sodium citrate, 0.05% Tween 20, pH 6.0), then returned to room temperature, subsequently rinsed 10 times in distilled water, then washed for 5 minutes in PBS. Sections were blocked with 1% BSA in PBS for 1 hour at room temperature then incubated with primary antibodies against ARL13B (1:300; Proteintech®_17711-1-AP) or acetylated a-tubulin (1:4000; Sigma T6793) or fibronectin (1:400; Sigma F3648), overnight at 4° C. Sections were washed three times in PBS, then incubated with the secondary antibodies conjugated to AlexaFluor § 594 (1:500; Invitrogen by Thermo Fisher Scientific®) for 1 hour at room temperature. Sections were then washed three times in PBS, and finally mounted with Fluoromount G with DAPI.

For immunodetection of laminin, rabbit polyclonal anti-laminin (Dako®2, Z0097) was used at 1:200 dilution overnight at 4° C. as primary antibody and anti-rabbit Ig-Alexa555 (Life Technologies §) was used as secondary antibody at 1:200 dilution for 3 hours at room temperature. After immunolabeling in wholemount conditions, the samples were embedded in Cryomatrix resin (Thermo Scientific®) and sectioned using a Cryostar® NX50 cryostat (Thermo Scientific (2) to obtain 14 µm sections which were mounted on microscopic slides (Thermo Scientific (9) in a mounting medium with NucBlue & counterstain (Thermo Fisher®) and imaged subsequently.

Brightfield and Epifluorescent Microscopy

Fluorescent imaging of the in vitro renal epithelial tissue was performed on a Zeiss Axio Observer Z1 ® inverted microscope with 40× EC Plan-Neofluar & objective and Zeiss AxioCam® MRm CCD camera. Alternatively, immuno- and histological stained sections were imaged using a Nikon 80i microscope with a Nikon® DS-Fil camera Transmission Electron Microscopy Renal epithelial tubules embedded in collagen or fibrin gel, were fixed in 4% paraformaldehyde/2% glutaraldehyde, then post-fixed in osmium tetroxide. Samples were dehydrated in a graded series of ethanol and propylene oxide, and embedded in EMbed 812 resin. Semi-thin sections were cut with a diamond histo knife, stained with toluidine blue, and selected for thinning Thin sections were cut with a diamond histo knife and placed on copper grids that were then stained with uranyl acetate and lead citrate. Samples were viewed and imaged using a JEOL JEM-1400 transmission electron microscope equipped with a Lab6 ® gun.

Scanning Electron Microscopy

Samples were fixed in 4% paraformaldehyde/2% glutaraldehyde, and then washed 3 times, each for 10 minutes, with 0.1 M Na-cacodylate buffer, pH 7.4. Samples were post-fixed for 30 minutes in 1% OsO4 in 0.1 M Na-cacodylate buffer. Samples were dehydrated using an ethanol series, followed by hexamethyldisilazane (HMDS; Electron Microscopy Sciences (2). Samples were then mounted onto metal stubs and sputter coated with gold. Samples were viewed and imaged digitally using a Hitachi® S-2700 Scanning Electron Microscope which was equipped with a Quartz PCI digital capture.

Live Cell Imaging

Time-lapse recordings of kidney epithelial cells in hydrogel tunnels were performed on a Zeiss Axio Observer Z1 ® inverted microscope with a 10× Plan Neofluar® objective. The microscope was equipped with a Marzhauser SCAN-IM powered stage and a Zeiss AxioCam® MRm CCD camera. Cell cultures established in flow chambers within cell culture dishes (Greiner) were continuously kept in a stage-incubator (Cell Movie) providing 37° C. and humidified 5% CO2 atmosphere. Stage positioning, focusing and image collection were all controlled by Zeiss Axiovision® 4.8 software and a custom-made experiment manager software module. Phase contrast images were collected consecutively in every 10 minutes from several microscopic fields for up to 4 days. Alternatively, for real-time video microscopy the images were captured at a rate of 20 frames per second.

Contraction Analysis

Contraction of renal tubule models were analyzed on the basis of image series captured by phase-contrast time-lapse video microscopy. Using NIH ImageJ software's Reslice function image series were resliced along a cross sectional line across the tubule resulting in a kymogram.

Cell Contractility Inhibitor

For inhibition of actomyosin contractility, Y27632, a cell-permeable Rho kinase inhibitor, (Merck Millipore (9) was applied. The inhibitor was dissolved in water and kept in 10 mM stock solutions and used at 50 µM final concentration. For control treatments, an identical volume of water was applied.

Kidney Tubule Model Device

An example of the tubular flow chamber device 100 is a polylactic acid (PLA) structure 102 having a round container arena 104 and two opposite ports 106, 108 that are 3D-printed into a 35 mm cell culture dish 110 (FIG. 1A). The arena 104 is filled with a hydrogel substance 112 surrounding a 6 mm long and 200-500 µm diameter tunnel mask 114 that spans the arena 104 and connects the two ports 106, 108 (FIG. 1B). The hydrogel 112 can be a type I collagen gel, a fibrin gel, or other combinations of extracellular matrix (ECM) proteins that are known. The mechanical characteristics of the hydrogel 112 are determined by the ECM protein type and its concentration, as well as regions of inhomogeneity, bubbles or other features. After removing the masking material 114, the hydrogel tunnel (114) is submerged in cell culture medium and seeded with renal epithelial cells 116 (FIG. 1B).

As can be seen in FIG. 1C, an input device 118, which can range from a pipette, syringe, inlet conduit from pump system, or other input is used. As shown the pipette configured input device 118 is inserted into the inlet port 108 to introduce cells 116 into the device 100 so as to go into the tunnel 114. Once in the tunnel, the cells 116 can form a monolayer and the cell structures, such as bulges or cysts.

The structure 102 is kept under standard cell culture conditions, whereby epithelial cells (e.g., cells 116) migrate and proliferate within the tunnel 114, covering its surface as a cell monolayer 116a as shown in FIGS. 1D-1E. Devices can be placed in a microscope stage-top cell culture incubator and subjected to live imaging, as shown in FIGS. 1C-1D. The morphology and motility of the cells 116, as well as changes in the size and shape of the renal tubule model lumen (e.g., tunnel 114) can be observed and recorded with live imaging microscopy for several days (FIG. 1D-E).

Cells 116 lining the tunnel 114 on the wall can be exposed to hydrodynamic shear forces by connecting the device to a circulatory flow (FIG. 1D): a peristaltic pump 120 pulls the medium from one of the ports (e.g., shown as outlet 116) via the conduit 122, and returns to the reservoir inside the culture dish 110. Thus, the flow of medium in the tunnel 114 of the renal tubule model is controlled by the rotational speed of a peristaltic pump 120.

As an example, the peristaltic pump flow rate of $\varphi=0.66$ µL/s yields a flow speed of $v=1.3$ mm/s in the tubule. If the viscosity of the medium is $\eta \approx 1$ mPa, the corresponding shear stress at the walls of a $d=650$ µm wide tunnel is $\tau=32\eta\varphi/d^3\pi\approx 24$ mPa. In comparison, a collecting duct tubule diameter is $d=20$-$50$ µm, and a $\varphi\approx 1$ µL/h filtrate flow rate translates to an average flow velocity of $v\approx 4\varphi/d^2\pi\approx 0.6$-$3$ mm/see and a corresponding wall shear stress of $\tau\approx 20$-$300$ mPa. Thus, flow velocities and wall shear stresses in the kidney tubule model are within the physiological range.

As shown, FIGS. 1A-1E illustrate the flow chamber device for a renal tubule model. FIG. 1A shows the flow chamber device 3D-printed in a cell culture dish, with scale bar: 10 mm.

FIG. 1B shows the device having the hydrogel tunnel, with scale bar: 1 mm. FIG. 1C includes a schematic diagram of cell seeding into the hydrogel tunnel of flow chamber using a pipette tip at one of the chamber's ports. FIG. 1D includes a schematic diagram of a medium circulation system in the kidney tubule mimetic device. FIG. 1E shows the hydrogel tunnel in the flow chamber with phase-contrast images of the bottom (left) and top (right) of a tunnel lined by M1 renal epithelial cells, with scale bar: 100 µm.

Epithelial Morphology

The device included seeded collagen I and fibrin gel tunnels with either M1 mouse cortical collecting duct cells or MDCK canine distal tubule cells. After two weeks in culture, the cells were characterized in the epithelium layer that developed in the kidney tubule mimetic. Histology and toluidine blue staining of semi-thin sections revealed a cell monolayer with a basement membrane (see FIGS. 2A-2C).

Figure 2A:
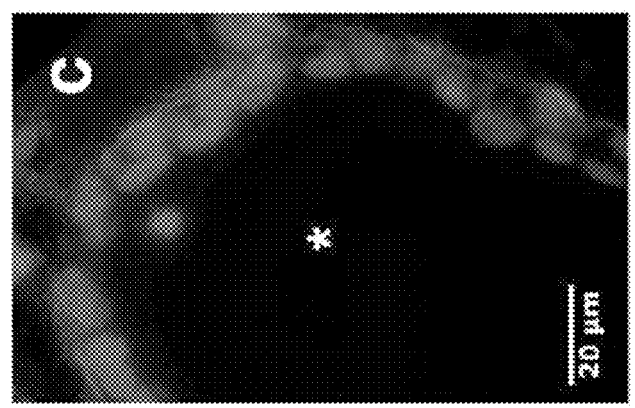
FIG. 2A is an image of a cross section of MDCK tubule in collagen I gel matrix from toluidine blue staining.
Figure 2B:
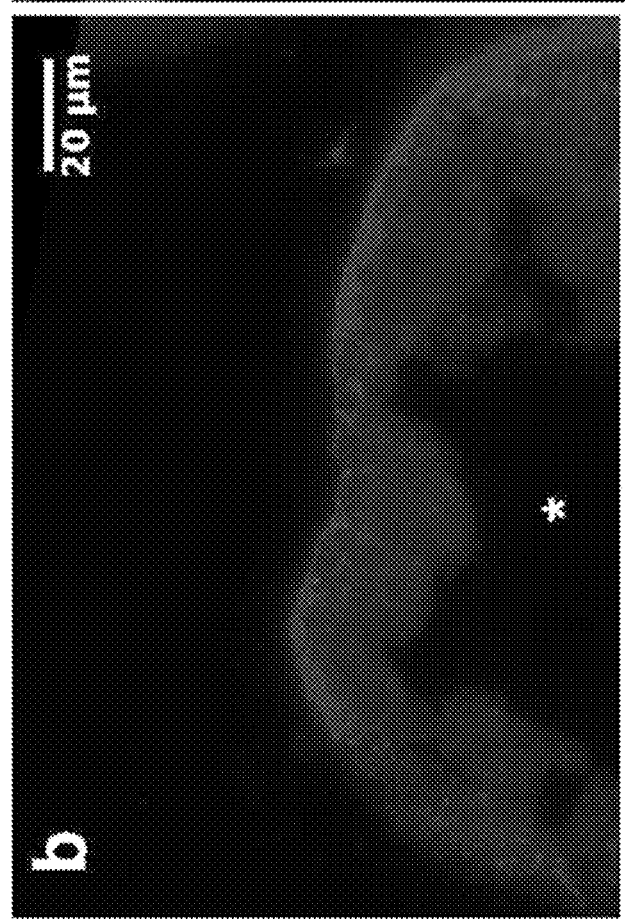
FIGS. 2B-2C show the immunofluorescence labeling of basement membrane proteins in tubules of M1 cells: laminin (FIG. 2B) and fibronectin (FIG. 2C).
Figure 2C:
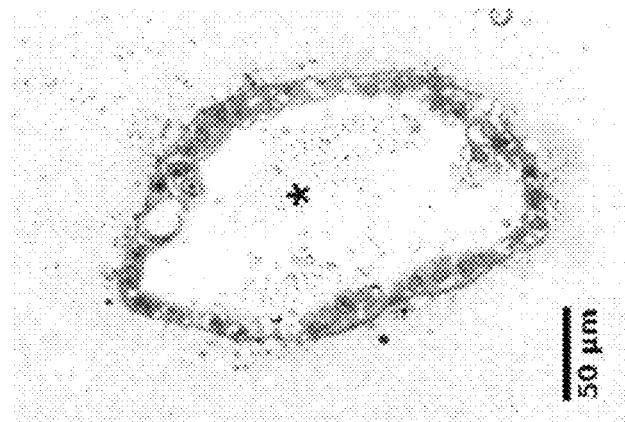

Immunolabeling of sections revealed that the basement membrane was rich in laminin and fibronectin. These ECM components were secreted and assembled by the renal epithelial cells on the basal side of cells. On the apical surface projecting into the tubular lumen, epithelial cells sprouted a primary cilium, which was immunostained for acetylated alpha-tubulin, marking the microtubular axoneme, or for Arl13B, marking the ciliary membrane (See FIGS. 2D-2E). Transmission electron microscopy (TEM) showed the presence of microvilli also on the apical surface of cells (FIG. 2F). Scanning electron microscopy (SEM) showed microvilli as well as doming of the apical surface of renal epithelial cells (FIG. 2G).

Figure 2H:
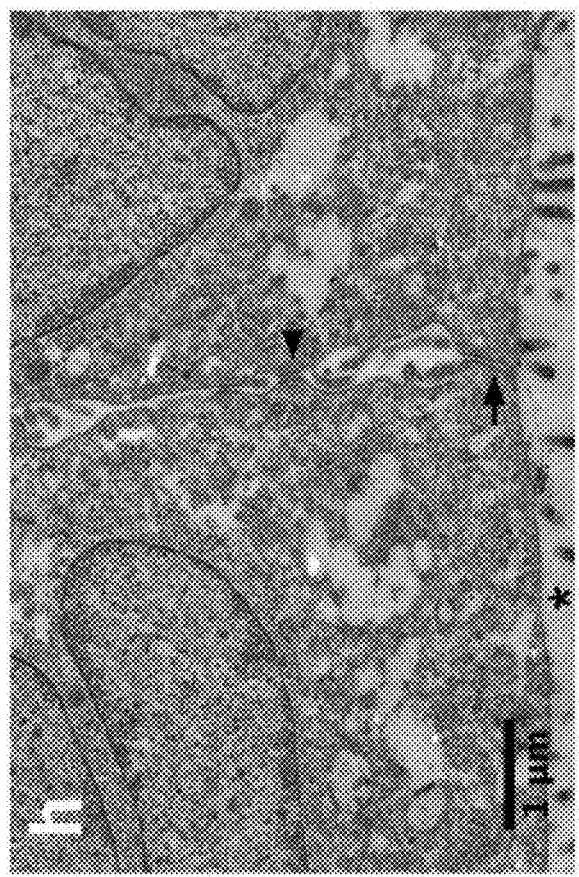
FIG. 2H includes a TEM image of MDCK cells that shows tight junctions and desmosomes.
Figure 2G:
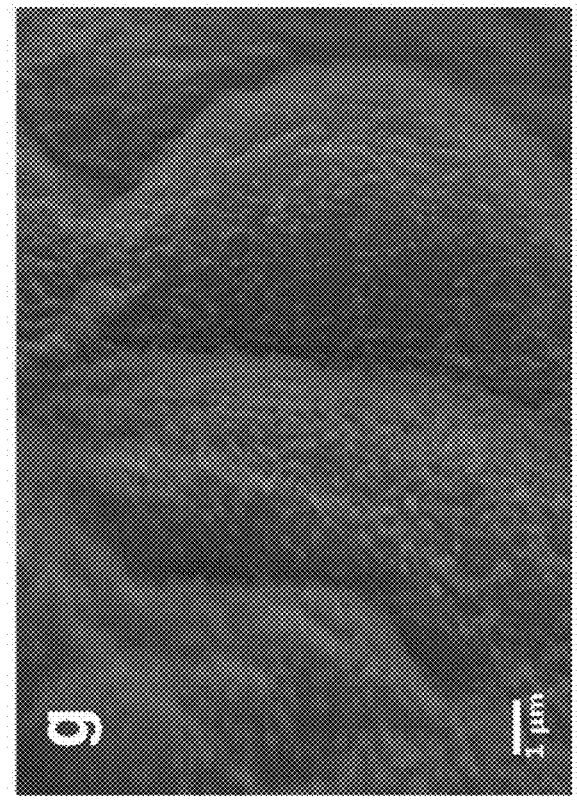
FIG. 2G includes an SEM image that shows doming of MDCK cells and microvilli on the apical surface.

Finally, TEM showed tight junctions connecting adjacent cells (FIG. 2H). The data indicate that in the mimetic tubes, renal epithelial cells form a monolayer with proper epithelial polarity and morphology.

FIGS. 2A-2H show the analysis of the histology of the renal tubule model. FIG. 2A is an image of a cross section of MDCK tubule in collagen I gel matrix. FIGS. 2B-2C show the immunofluorescence labeling (whitish color) of basement membrane proteins in tubules of M1 cells: laminin (FIG. 2B) and fibronectin (FIG. 2C).

FIGS. 2D-2E show the immunolocalization (whitish) of primary cilia on M1 cells (arrows) —acetylated alpha-tubulin in FIG. 2D, Arl13B in FIG. 2E. FIG. 2F shows a TEM image of M1 cells, with an arrow points to microvilli. FIG. 2G includes an SEM image that shows doming of MDCK cells and microvilli on the apical surface. FIG. 2H includes a TEM image of MDCK cells that shows tight junctions (arrow) and desmosomes (arrowhead). The scale bars are listed in the figures, and the asterisks indicate the tubule lumen in FIGS. 2A-2H.

To characterize the epithelium developing within the kidney tubule mimetic device, collagen I and fibrin gel tunnels were seeded with either M1 human collecting duct epithelial cells or canine collecting duct (MDCK) cells. After two weeks in culture, tubules were fixed and subjected to physical sectioning. Both histology and toluidine blue staining of semi-thin sections revealed a cell monolayer with a basement membrane.

Immunolabeled sections indicate that the basement membrane is rich in laminin and fibronectin. These ECM components were secreted and assembled by the renal epithelial cells, and are enriched at the basal side of the cells. On the opposite, apical surface projecting into the tubular lumen, most renal epithelial cells possess a primary cilium, which is a small, sensory organelle implicated in various diseases including PKD. Positive staining with these antibodies revealed primary cilia at the apical surface of the epithelial cells. Consistent with the presence of primary cilia, transmission electron microscopy (TEM) showed a singular slender extension on the apical surface of cells. TEM and scanning electron microscopy (SEM) also revealed microvilli on the apical surface. Finally, TEM showed tight junctions connecting adjacent cells. The data indicate that in the mimetic tubes renal epithelial cells form a monolayer with proper epithelial polarity and morphology.

Epithelium in Contractile State

To study the contractility of our mimetic renal tubule epithelium, the Rho kinase inhibitor Y27632 was used to reversibly inhibit actomyosin contractile function. The inhibitor was applied at 50 µM final concentration in the flow chamber without circulation, resulting in dilation of the tunnel within 30 minutes. Subsequent washout of the inhibitor caused a gradual contraction of the tunnel to approximately its initial state. Both the dilation and contraction responses were quantitatively analyzed by constructing kymograms from the phase-contrast time-lapse image series as shown in FIG. 3A. In a collagen I gel, the diameter of 250 µm wide M1- or MDCK-lined tunnels contracted by 20 or 15 µm, respectively as shown in FIG. 3B. The relative contraction (as defined by the ratio of the measured contraction to tubule diameter) is larger for tubules with smaller diameters: while the 250 µm tubule contracts almost 13% of its diameter, a 600 µm large tubule contracts only about 5% as shown in FIG. 3C.

FIGS. 3A-3C show the contractility of model renal tubules. FIG. 3A includes a representative kymogram along a perpendicular cross section of a tubule of M1 cells in collagen I gel matrix. Time progresses from top to bottom, a 10$h$ long interval is indicated by the arrow. The duration of treatment with 50 µM Y27632 Rho kinase inhibitor is indicated with the red line (scale bar: 50 µm). FIGS. 3B-3C include graphs illustrating quantitative analysis of tubule contractility. FIG. 3B shows the contraction of 250 µm diameter tubules of M1 or MDCK cells, embedded in collagen I gels (error bars indicate SEM, n=2). FIG. 3C shows the contraction of thin (250 µm) or wide (600 µm) tubules of M1 cells, expressed as percent of untreated tubule diameter. Error bars represent SEM.

Tubule Remodeling

The tubules can be maintained in the mimetic devices for 2-3 weeks or longer. During this time frame the kidney epithelial cells can interact with and remodel the surrounding hydrogel. When tubules are formed in the presence of features, such as low density regions or air bubbles on/in the lumen surface of the tunnel, kidney epithelial cells migrate into and line these features and form initial bulges on the tubule wall. During culture the initial buds further extend and form sphere-like extensions or protrusions along the tunnel wall as cells slowly expand into the surrounding ECM (FIGS. 4A-4E). Within such areas or features, epithelial cells are also often observed invading the hydrogel in multicellular sprouts. Thus, the kidney tubule mimetic device can be used to study epithelial patterning, including cyst formation, and its guidance by tissue mechanical factors.

Figure 4A:
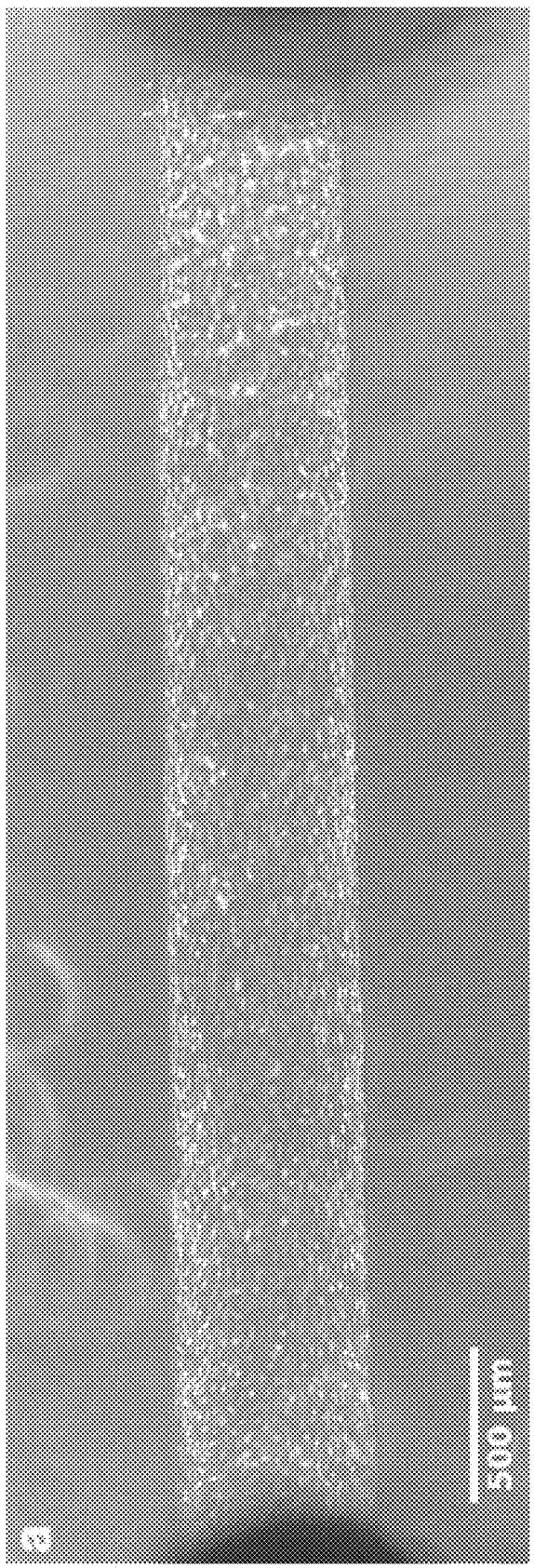
FIG. 4A includes a phase-contrast image of a full length straight tubule at 5 days in vitro (DIV 5).
Figures 4B, 4C, 4D:
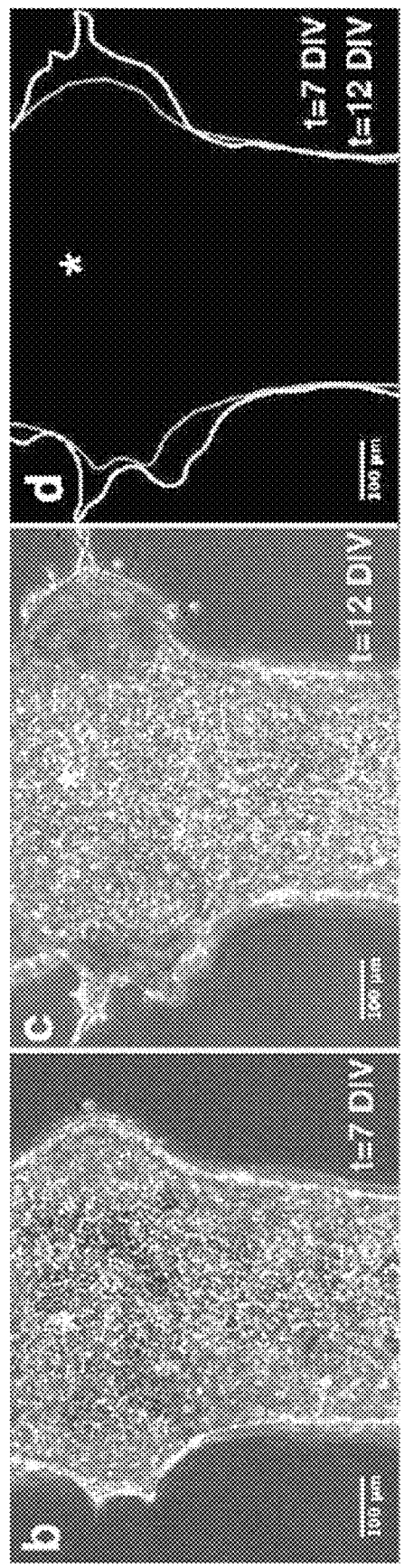
FIGS. 4B-4C include images of tubule with initial bulges in collagen I gel lined by M1 cells, which exhibits bud extensions, at DIV 7 (FIG. 4B) and DIV 12 (FIG. 4C).
FIG. 4D includes an analytical comparison of tubule wall outlines at DIV 7 (inner lines) and DIV 12 (outer lines).
Figure 4E:
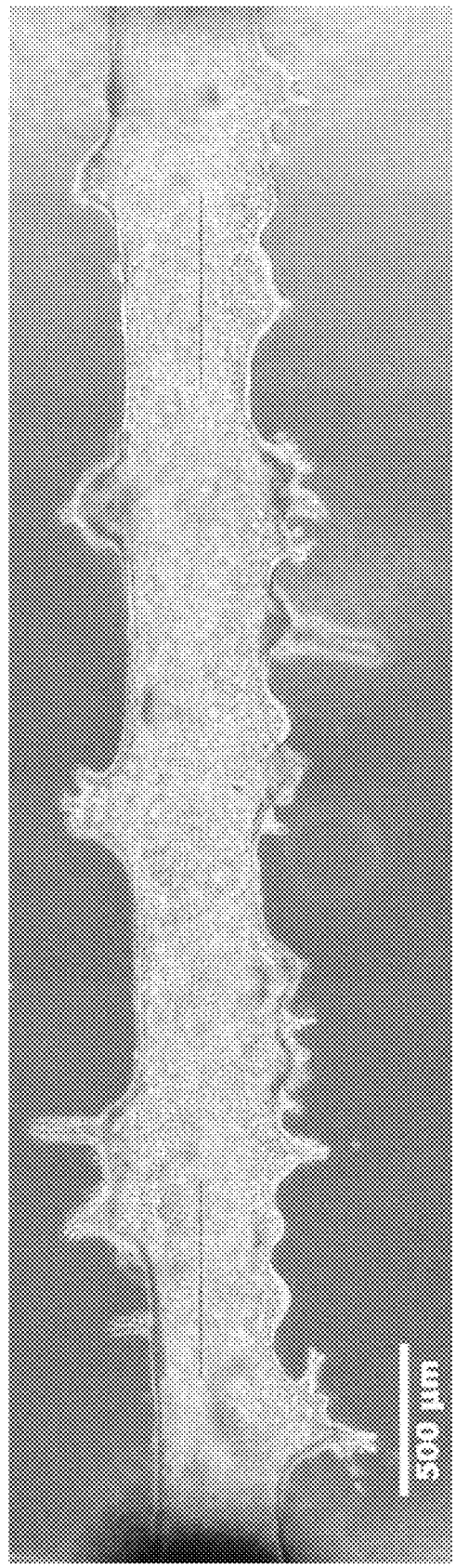
FIG. 4E shows the phase-contrast image of the full length budding tubule at DIV 16.

FIGS. 4A-4E show that the renal tubules can remodel the hydrogel and thereby change morphology, such as by introducing bulges, which can be at the features (e.g., bubble, low density region, or the like). FIG. 4A includes a phase-contrast image of a full length straight tubule at DIV 5, with scale bar: 500 µm. FIGS. 4B-4C include images of tubule with initial bulges in collagen I gel lined by M1 cells, which exhibits bud extensions, at DIV 7 (FIG. 4B) and DIV 12 (FIG. 4C). FIG. 4D includes an analytical comparison of tubule wall outlines at DIV 7 (inner lines) and DIV 12 (outer lines). The asterisks indicate tubule lumen, scale bar: 100 µm. FIG. 4E shows the phase-contrast image of the full length budding tubule at DIV 16, with scale bar: 500 µm.

One skilled in the art will appreciate that, for this and other processes and methods disclosed herein, the functions performed in the processes and methods may be implemented in differing order. Furthermore, the outlined steps and operations are only provided as examples, and some of the steps and operations may be optional, combined into fewer steps and operations, or expanded into additional steps and operations without detracting from the essence of the disclosed embodiments.

The present disclosure is not to be limited in terms of the particular embodiments described in this application, which are intended as illustrations of various aspects. Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds compositions or biological systems, which can, of course, vary. It is also to be understood that the terminology used herein is for the purpose of describing particular embodiments only, and is not intended to be limiting.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," and the like include the number recited and refer to ranges which can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth. From the foregoing, it will be appreciated that various embodiments of the present disclosure have been described herein for purposes of illustration, and that various modifications may be made without departing from the scope and spirit of the present disclosure. Accordingly, the various embodiments disclosed herein are not intended to be limiting, with the true scope and spirit being indicated by the following claims. All references recited herein are incorporated herein by specific reference in their entirety.

Praetorius, H. A. & Spring, K. R. The renal cell primary cilium functions as a flow sensor. Curr Opin Nephrol Hypertens 12, 517-20 (2003). DOI 10.1097/00041552-200309000-00006.

Liu, W. et al. Mechanoregulation of intracellular Ca2+ concentration is attenuated in collecting duct of monocilium-impaired orpk mice. Am J Physiol Renal Physiol 289, F978-88 (2005). DOI 10.1152/ajprenal.00260.2004.

Ferreira, R. R., Fukui, H., Chow, R., Vilfan, A. & Vermot, J. The cilium as a force sensor-myth versus reality. J Cell Sci 132 (2019). DOI 10.1242/jcs.213496.

Nigro, E. A. et al. Polycystin-1 Regulates Actomyosin Contraction and the Cellular Response to Extracellular Stiffness. Sci Rep 9, 16640 (2019). DOI 10.1038/s41598-019-53061-0.

Cordido, A., Besada-Cerecedo, L. & Garci'a-Gonzalez, M. A. The Genetic and Cellular Basis of Autosomal Dominant Polycystic Kidney Disease-A Primer for Clinicians. Front Pediatr 5, 279 (2017). DOI 10.3389/fped.2017.00279.

Kou, P., Wei, S. & Xiong, F. Recent Advances of mTOR Inhibitors Use in Autosomal Dominant Polycystic Kidney Disease: Is the Road Still Open? Curr Med Chem 26, 2962-2973 (2019). DOI 10.2174/0929867325666180330094434.

Maggiorani, D. et al. Shear Stress-Induced Alteration of Epithelial Organization in Human Renal Tubular Cells. PLOS One 10, e0131416 (2015). DOI 10.1371/journal.pone.0131416.

Freedman, B. S. et al. Reduced ciliary polycystin-2 in induced pluripotent stem cells from polycystic kidney disease patients with PKD1 mutations. J Am Soc Nephrol 24, 1571-86 (2013). DOI 10.1681/ASN.2012111089.

Homan, K. A. et al. Flow-enhanced vascularization and maturation of kidney organoids in vitro. Nat Methods 16, 255-262 (2019). DOI 10.1038/s41592-019-0325-y.

Lin, N. Y. C. et al. Renal reabsorption in 3D vascularized proximal tubule models. Proc Natl Acad Sci USA 116, 5399-5404 (2019). DOI 10.1073/pnas.1815208116.

Schutgens, F. et al. Tubuloids derived from human adult kidney and urine for personalized disease modeling. Nat Biotechnol 37, 303-313 (2019). DOI 10.1038/s41587-019-0048-8.

Rein, J. L. et al. Effect of luminal flow on doming of mpkCCD cells in a 3D perfusable kidney cortical collecting duct model. Am J Physiol Cell Physiol 319, C136-C147 (2020). DOI 10.1152/ajpcell.00405.2019.

Chapron, A. et al. An Improved Vascularized, Dual-Channel Microphysiological System Facilitates Modeling of Proximal Tubular Solute Secretion. ACS Pharmacol Transl Sci 3, 496-508 (2020). DOI 10.1021/acsptsci.9b00078.

Stoos, B. A., Naray-Fejes-Tóth, A., Carretero, O. A., Ito, S. & Fejes-Tóth, G. Characterization of a mouse cortical collecting duct cell line. Kidney Int 39, 1168-75 (1991). DOI 10.1038/ki.1991.148.

Helm, C.-L. E., Fleury, M. E., Zisch, A. H., Boschetti, F. & Swartz, M. A. Synergy between interstitial flow and VEGF directs capillary morphogenesis in vitro through a gradient amplification mechanism. Proc Natl Acad Sci USA 102, 15779-84 (2005). DOI 10.1073/pnas.0503681102.

Gulyas, M., Csiszer, M., Mehes, E. & Czirok, A. Software tools for cell culture-related 3D printed structures. PLOS One 13, e0203203 (2018). DOI 10.1371/journal.pone.0203203.

Magenheimer, B. S. et al. Early embryonic renal tubules of wild-type and polycystic kidney disease kidneys respond to cAMP stimulation with cystic fibrosis transmembrane conductance regulator/Na (+),K (+),2Cl (−) Co-transporter-dependent cystic dilation. J Am Soc Nephrol 17, 3424-37 (2006). DOI 10.1681/ASN.2006030295.

Maser, R. L., Magenheimer, B. S. & Calvet, J. P. Metanephric organ culture. Methods Cell Biol 153, 169-183 (2019). DOI 10.1016/bs.mcb.2019.04.018.

Sharma, M., Reif, G. A. & Wallace, D. P. In vitro cyst formation of ADPKD cells. Methods Cell Biol 153, 93-111 (2019). DOI 10.1016/bs.mcb.2019.05.008.

Freedman, B. S. et al. Modelling kidney disease with CRISPR-mutant kidney organoids derived from human pluripotent epiblast spheroids. Nat Commun 6, 8715 (2015). DOI 10.1038/ncomms9715.

Yengej, F. A. Y., Jansen, J., Rookmaaker, M. B., Verhaar, M. C. & Clevers, H. Kidney Organoids and Tubuloids. Cells 9 (2020). DOI 10.3390/cells9061326.

Jimenez-Torres, J. A., Peery, S. L., Sung, K. E. & Beebe, D. J. LumeNEXT: A Practical Method to Pattern Luminal Structures in ECM Gels. Adv Healthc Mater 5, 198-204 (2016). DOI 10.1002/adhm.201500608.

Czirok A, Rupp PA, Rongish BJ, Little CD. Multi-field 3D scanning light microscopy of early embryogenesis. J Microsc. 2002;206 (Pt 3): 209-17. Epub 2002 Jun. 18. doi: 10.1046/j.1365-2818.2002.01032.x. PubMed PMID: 12067365.

Zamir EA, Czirok A, Rongish BJ, Little CD. A digital image-based method for computational tissue fate mapping during early avian morphogenesis. Ann Biomed Eng. 2005;33 (6): 854-65. Epub 2005 Aug. 5. doi: 10.1007/s10439-005-3037-7. PubMed PMID: 16078625.

Zamir EA, Czirok A, Cui C, Little CD, Rongish BJ. Mesodermal cell displacements during avian gastrulation are due to both individual cell-autonomous and convective tissue movements. Proc Natl Acad Sci USA. 2006;103 (52): 19806-11. Epub 2006 Dec. 21. doi: 10.1073/pnas.0606100103. PubMed PMID: 17179040; PMCID: PMC1705812.

Szabo A, Rupp PA, Rongish BJ, Little CD, Czirok A. Extracellular matrix fluctuations during early embryogenesis. Phys Biol. 2011; 8 (4): 045006. Epub 2011 Jul. 14. doi: 10.1088/1478-3975/8/4/045006. PubMed PMID: 21750366; PMCID: PMC3176676.

Rupp PA, Rongish BJ, Czirok A, Little CD. Culturing of avian embryos for time-lapse imaging. Biotechniques. 2003; 34 (2): 274-8. Epub 2003 Mar. 5. doi: 10.2144/03342st01. PubMed PMID: 12613250.

Aleksandrova A, Rongish BJ, Little CD, Czirok A. Active cell and ECM movements during development. Methods Mol Biol. 2015; 1189:123-32. Epub 2014 Sep. 24. doi: 10.1007/978-1-4939-1164-6_9. PubMed PMID: 25245691; PMCID: PMC4401075.

Pongor L, Harami-Papp H, Mehes E, Czirok A, Gyorffy B. Cell Dispersal Influences Tumor Heterogeneity and Introduces a Bias in NGS Data Interpretation. Scientific reports. 2017;7 (1): 7358. Epub 2017 Aug. 6. doi: 10.1038/841598-017-07487-z. PubMed PMID: 28779157; PMCID: PMC5544774.

The invention claimed is:

1. A renal tube assay device comprising:
a container having an inlet port and an outlet port;
a matrix material in the container, therein the container is located in a cell culture dish; and
a lumen in the matrix material extending from the inlet port to the outlet port,
wherein the lumen includes a luminal surface with at least one low density region that has a lower density compared to another adjacent region of the matrix material that is located at least partially around the at least one low density region.

2. The renal tube assay device of claim 1, wherein the at least one low density region has a form of a bubble.

3. The renal tube assay device of claim 1, wherein the inlet port and/or outlet port is adapted for receiving a pipette tip.

4. The renal tube assay device of claim 1, wherein the matrix material includes a hydrogel.

5. The renal tube assay device of claim 1, wherein the low density region bulges into the lumen.

6. The renal tube assay device of claim 1, comprising a cell culture in the lumen.

7. The renal tube assay device of claim 1, comprising a cell culture in the at least one low density region, thereby forming a bulge structure.

8. The renal tube assay device of claim 1, comprising a renal cell culture in the lumen with cells in the at least one low density region, thereby forming a bulge structure.

9. A renal tube assay system comprising:
the renal tube assay device of claim 1; and
a fluidic flow system including at least one pump fluidly coupled with at least one of the inlet port or outlet port wherein the at least one pump is coupled with a conduit that extends into a cell culture dish having the renal tube assay device in cell culture media.

10. The renal tube assay system of claim 9, further comprising an analytical system operably coupled with the lumen in the matrix material.

11. The renal tube assay system of claim 10, wherein the analytical system is an optical system having at least one optical device configured for acquiring images or video of the lumen.

12. The renal tube assay system of claim 9, further comprising a rotational system having a rotational mechanism coupled to the container such that the container rotates with rotation of the rotational mechanism.

13. A method of forming a bulge cell culture in a renal tube construct, comprising:
providing the renal assay system of claim 9, and therein and culturing renal cells in the lumen and in the at least one low density region to form a bulge in the matrix material with the renal cells.

14. The method of claim 13, comprising rotating the container and matrix material to rotate the lumen and renal cells therein.

15. A method of studying a bulge cell culture in a renal tube construct, comprising:
providing the renal assay system of claim 9, and therein:
culturing renal cells in the lumen and in the at least one low density region to form a bulge in the matrix material with the renal cells;
pumping a media fluid through the lumen; and
monitoring the cells in the lumen and bulge.

16. The method of claim 15, wherein the monitoring is optical monitoring with an optical system.

17. A method of studying activity of an agent in a renal tube construct, comprising:
providing the renal assay system of claim 9, and therein:
culturing renal cells in the lumen and in the at least one low density region to form a bulge in the matrix material with the renal cells;
pumping a media fluid containing the agent through the lumen; and
monitoring the cells in the lumen and bulge.

18. A method of forming the renal tube assay device of claim 1, comprising:
- forming a container having an inlet port and an outlet port;
- forming a matrix material in the container around a lumen material, wherein the matrix material is formed to include at least one low density region that has a lower density compared to another adjacent region of the matrix material that is located at least partially around the at least one low density region;
- vortexing or bubbling a gas through the matrix material during formation; and
- withdrawing the lumen material to form a lumen in the matrix material extending from the inlet port to the outlet port, wherein the lumen includes a luminal surface with at least one of the low density regions.

19. The method of claim 18, comprising culturing renal cells in the lumen and in the at least one low density region to form a bulge in the matrix material with the renal cells.

20. The method of claim 19, comprising rotating the container and matrix material to rotate the lumen and renal cells therein.

* * * * *